US011330995B2

(12) United States Patent
Fujii et al.

(10) Patent No.: US 11,330,995 B2
(45) Date of Patent: May 17, 2022

(54) APPARATUS AND METHOD FOR IMAGING AND ANALYZING HEMODYNAMICS

(71) Applicant: SOFTCARE CO., LTD., Fukuoka (JP)

(72) Inventors: Hitoshi Fujii, Fukuoka (JP); Kenji Okamoto, Fukuoka (JP); Phuong Thuy Le, Tochigi (JP); Noriyoshi Takahashi, Fukuoka (JP); Takeshi Shirakawa, Fukuoka (JP); Tetsu Kuroki, Fukuoka (JP)

(73) Assignee: SOFTCARE CO., LTD., Fukutsu (JP)

( * ) Notice: Subject to any disclaimer, the term of this patent is extended or adjusted under 35 U.S.C. 154(b) by 421 days.

(21) Appl. No.: 15/568,272

(22) PCT Filed: Nov. 24, 2016

(86) PCT No.: PCT/JP2016/084746
§ 371 (c)(1),
(2) Date: Oct. 20, 2017

(87) PCT Pub. No.: WO2018/003139
PCT Pub. Date: Jan. 4, 2018

(65) Prior Publication Data
US 2018/0206740 A1    Jul. 26, 2018

(30) Foreign Application Priority Data
Jun. 28, 2016   (JP) .............................. JP2016-127441

(51) Int. Cl.
*A61B 5/026*     (2006.01)
*A61B 5/0245*    (2006.01)
(Continued)

(52) U.S. Cl.
CPC ............ *A61B 5/0261* (2013.01); *A61B 5/026* (2013.01); *A61B 5/02028* (2013.01);
(Continued)

(58) Field of Classification Search
CPC ..... A61B 5/026; A61B 3/1233; A61B 3/1241; A61B 5/02028; A61B 5/02042;
(Continued)

(56) References Cited

U.S. PATENT DOCUMENTS 6,984,207 B1 * 1/2006 Sullivan ............... A61B 5/0002
600/300
2009/0099424 A1 * 4/2009 O'Brien ............. A61B 5/02028
600/301
(Continued)

FOREIGN PATENT DOCUMENTS

| JP | H4-242628 A | 8/1992 |
|---|---|---|
| JP | H5-28133 B | 4/1993 |
| JP | H5-28134 B2 | 4/1993 |
| JP | H8-112262 A | 5/1996 |
| JP | 2003-84019 A | 3/2003 |
| JP | 2003-164431 A | 6/2003 |

(Continued)

*Primary Examiner* — Patrick Fernandes
(74) *Attorney, Agent, or Firm* — McGlew and Tuttle, P.C.

(57) ABSTRACT

The present invention images a heartbeat strength representing the strength of pulsations (beats) on a map as a new dynamics index different from the conventional waveform numerical value. A computation section according to the present invention obtains, from time-course changes of the blood flow map obtained as a result of computation of blood flow speed, a signal intensity at a fundamental frequency determined from time-series blood flow data within a predetermined region, and calculates a heartbeat strength which represents the strength of heartbeats on the basis of the signal intensity. A display section images and displays the heartbeat strength calculated by the heartbeat strength computation section. Also, the display section displays the heartbeat strength calculated by the heartbeat strength computation section by superimposing the heartbeat strength on a combined map created by averaging a plurality of blood flow maps arranged in a chronological order.

1 Claim, 16 Drawing Sheets

(51) Int. Cl.
*A61B 5/02* (2006.01)
*A61B 5/145* (2006.01)
*A61B 5/00* (2006.01)

(52) U.S. Cl.
CPC ........ *A61B 5/0245* (2013.01); *A61B 5/14535* (2013.01); *A61B 5/0075* (2013.01); *A61B 5/0077* (2013.01)

(58) Field of Classification Search
CPC ... A61B 6/507; A61B 5/14535; A61B 5/0077; A61B 5/0261; A61B 5/0245; A61B 5/0075
See application file for complete search history.

(56) References Cited

U.S. PATENT DOCUMENTS

| | | | |
|---|---|---|---|
| 2010/0056936 A1* | 3/2010 | Fujii | A61B 3/1241 600/504 |
| 2012/0190967 A1* | 7/2012 | Nahm | A61B 6/504 600/411 |
| 2016/0278718 A1 | 9/2016 | Fujii et al. | |

FOREIGN PATENT DOCUMENTS

| | | |
|---|---|---|
| JP | 2003-180641 A | 7/2003 |
| JP | 2010-178933 A | 8/2010 |
| WO | 2008/069062 A1 | 6/2008 |
| WO | 2014/175154 A1 | 10/2014 |

\* cited by examiner

STATE OF MAP IN WHICH COMBINED MAP AND
HEARTBEAT STRENGTH MAP ARE SUPERIMPOSED
(WHEN PATIENT SUFFERS FROM GOUT)

FIG. 7

```
# load required library
library(lars)
library(glmnet)

# The stored data-set is dt.
# dt$Time.s. : Time[sec] is stored the time on blood flow map.
# dt$MBR.RB1  : MBR is calulated average of Region of interest on blood
flow map.
mat : Fourier transfer matrix set dataframe
d1 <- data.frame(V1=dt$Time.s.,V2=dt$MBR.RB1)

# LASSO analysis
nf <- 100
divf <- 10
n <- 2*nf
df <- divf/nf
f <- seq(df,divf,df)
t <- 1/f y <- d1$V2 - mean(d1$V2)
a <- glmnet(mat, y, alpha=1)
ndim <- a$dim[2]
nd <- length(t)
pow <- matrix( 0, nd, ndim)
for ( i in 1:ndim)
{
        v <- a$beta[,i]
        for ( j in 0:1)
        {
                pow[,i] <- pow[,i] + v[(nd*j+1):(nd*(j+1))]^2
        }
}
res <- list(pow=pow,lambda=a$lambda)
class(res) <- c("lasso_power",class(res))

Figures and plots
plot(d1,xlab="Time", ylab="Flux",pch=16,cex=0.8)
plot(f,res$pow[,length(res$lambda)],xlim=c(0,6),type="l",col="red",xlab="F
requency",ylab="Power")
```

BLOOD FLOW DATA OF REGION OF INTEREST 1

PREDICTED POWER SPECTRUM CREATED ON THE BASIS
OF BLOOD FLOW DATA OF REGION OF INTEREST 1

BLOOD FLOW DATA OF REGION OF INTEREST 2

PREDICTED POWER SPECTRUM CREATED ON THE BASIS
OF BLOOD FLOW DATA OF REGION OF INTEREST 2

STATE OF MAP IN WHICH COMBINED MAP
AND HEARTBEAT STRENGTH MAP ARE SUPERIMPOSED
(WHEN GOUT HAS REMITTED)

BLOOD FLOW DATA OF REGION OF INTEREST 1

PREDICTED POWER SPECTRUM CREATED ON THE BASIS
OF BLOOD FLOW DATA OF REGION OF INTEREST 1

SCHEMATIC OVERALL CONFIGURATION

EXAMPLE OF CREATION OF COMBINED MAP

TO COMBINED MAP (FIG. 20)

TIME-COURSE CHANGES OF BLOOD FLOW
DURING SINGLE HEARTBEAT

COMBINED MAP

EXAMPLE OF CREATION OF COMBINED MAP

SUPERIMPOSE SEPARATION MAP ONTO COMBINED MAP

APPARATUS AND METHOD FOR IMAGING AND ANALYZING HEMODYNAMICS

TECHNICAL FIELD

The present invention relates to an apparatus and a method for imaging and analyzing hemodynamics which apply laser light to a biotissue having blood cells, and measure and image the speed of blood flow on the basis of a speckle signal reflected from the biotissue, and in which, for each region of interest, the strength of pulsation (beat) of the blood flow waveform is digitized (evaluated by a numerical value) for image diagnosis.

BACKGROUND ART

In a conventional blood flow speed measurement apparatus, laser light is applied to a biotissue having blood cells such as the eyeground or the skin, and a so-called speckle image (an image of random speckle pattern formed as a result of interference of reflection light from the blood cells) is led onto an image sensor such as a solid state imaging device (CCD or CMOS). A large number of speckle images are successively captured and stored at predetermined intervals. A predetermined number of images are selected from the large number of stored images, a value which reflects the speed of a time-course change in the output of each pixel throughout the images is calculated, and the speed of blood cells (blood flow speed) is calculated from the calculated value. In a blood flow speed measurement apparatus of such a type, since the value indicating the output changing speed of each pixel corresponds to the moving speed of blood cells, the blood flow distribution in the biotissue can be color-disposed on a monitor screen as a two-dimensional image (a blood flow map) on the basis of the calculated value indicating the output changing speed of each pixel. A blood flow map observed in actuality is composed of a series of blood flow maps (hereinafter also referred to as "original maps") calculated at a speed of about 30 frames per sec, and can be displayed as a motion video. Therefore, the conventional blood flow speed measurement apparatus has been put to practical use as an apparatus for observing the hemodynamics of the eyeground or skin (see Patent Documents 1 to 7).

Also, the present inventors have proposed a blood flow speed imaging apparatus (see Patent Document 8). In this apparatus, a series of original maps obtained through blood flow measurement performed for several seconds are used. Through utilization of the periodicity of pulsation (heartbeat) of the heart, averaging of corresponding original maps is performed from the beginning of each heartbeat so as to create averaged blood flow maps for one heartbeat (hereinafter referred to as "heartbeat maps"), and a change in blood flow within the pulsation for one heartbeat is analyzed in various regions within a field of observation view. A numerical value (i.e., the degree of distortion) is introduced for distinction between a region having a sharp rising waveform attributable to the arterial blood flow and a region having a mildly rising and falling waveform attributable to the venous blood flow. Thus, the apparatus can display on the blood flow maps a region which pulsates due to the arterial blood flow and a region which pulsates due to the venous blood flow.

Moreover, the present inventors have added a new blood flow image diagnosing function to the conventional apparatus. Specifically, its computation section has an additional function of performing an averaging process for a plurality of blood flow map data sets for one or more heartbeats so as to average all the original maps to thereby create a blood flow map (hereinafter referred to as a "combined map") having no time information, and separating, from this combined map, a blood flow within a surface blood vessel within an observation region of a biotissue and the background blood flow therearound. These blood flows are displayed on the combined map on a display section in a distinguishable manner. Various variables which characterize the blood flow waveforms of the separated regions are defined, and these variables are compared for clinical diagnosis (see Patent Document 8). In the following description, an apparatus having such a function added thereto will be referred to as a "hemodynamics imaging and diagnosing apparatus."

Such a conventional hemodynamics imaging and diagnosing apparatus will now be described with reference to FIGS. 15 to 24. FIG. 15 is a schematic overall configuration of a hemodynamics imaging and diagnosing apparatus configured on the basis of the conventional technique (see Patent Document 8). A laser light irradiation system 2 applies laser light to a biotissue 1 (for example, the dorsum of foot) through a half mirror 3. A light receiving section 4 receives laser reflection light and forms an image of the biotissue on a solid state imaging device. The light receiving section 4 driven on the basis of a timing pulse 6 converts the biotissue image formed by a light receiving lens to an electrical signal on the basis of the timing pulse 6, reads out the signal charge in a frame storage mode, amplifies it as a video signal, and outputs the amplified video signal.

An image capturing section 5 successively captures a plurality of images represented by the output video signal. A storage section 7 stores the captured images. A computation section 8 computes the blood flow speed within the biotissue from time-course changes in the output signals of corresponding pixels throughout the plurality of stored images. A display section 9 can display a two-dimensional distribution information in the form of a map in which the information of the blood flow map obtained from the computation section 8 is displayed, and other pieces of information such as waveform numerical values are superimpose on the blood flow map.

FIG. 16 is a diagram showing the specific configuration of the computation section 8 according to the conventional technique. A blood flow analysis section 11 analyzes the images fetched from the image storage section 7 and creates a blood flow map in which the blood flow distribution in the biotissue is displayed as a two-dimensional image. The blood flow map is obtained by computing the change rates of the light intensities of corresponding pixels of the plurality of fetched images and mapping the change rates, and the blood flow map reflects the movement of blood cells. Each pixel on the blood flow map has a blood flow value. The blood flow value becomes large in a region where the movement of blood cells is fast and becomes small in a region where the movement of blood cells is slow. As described above, the image storage section 7 successively stores a plurality of images at predetermined time intervals of one heart beat, two heart beat, or longer (intervals of 1/30 sec in the example). The blood flow speed in the organism is computed from time-course changes of the output signals of corresponding pixels throughout the plurality of stored images. In FIG. 17, this computed blood flow value is shown as time-course changes of blood flow. In general, the blood flow value pulsates. Each of (four) arrows a on the upper side of FIG. 17 shows the temporal position of a lowest blood flow map in each pulsation.

A heartbeat analysis section 12 analyzes the blood flow map from the blood flow analysis section 11. Namely, the heartbeat analysis section 12 searches a blood flow map having the lowest blood flow value for each pulsation, from an averaged blood flow value within a region of interest for each of the chronologically stored blood flow map, thereby determining the lowest blood flow map for each heartbeat. In FIG. 18, the image of the blood flow map having the lowest blood flow value is shown as a leading map e. The determined blood flow map is sent to a heartbeat map creation section 13.

FIG. 17 shows time-course changes in blood flow in the case where the apparatus has succeeded in heartbeat detection. In the exemplified case, pulsations b, c, and d corresponding to three hearts are observed. A series of maps f shown in FIG. 18 is a plurality of blood flow maps in the period of time of the pulsation b, a series of maps g shown in FIG. 18 is a plurality of blood flow maps in the period of time of the pulsation c, and a series of maps h shown in FIG. 18 is a plurality of blood flow maps in the period of time of the pulsation d. FIG. 18 is an illustration used for describing a method of preparing a combined map from a plurality of blood flow maps corresponding to pulsations.

The heartbeat map creation section 13 first performs averaging for the corresponding pixels of the leading maps e of one, two, or more pulsations so as to create an averaged blood flow map i. Subsequently, the heartbeat map creation section 13 averages the second blood flow maps j in the respective pulsations, and averages the third blood flow maps k in the respective pulsations. The heartbeat map creation section 13 repeats the averaging operation up to the ends of the pulsations and finally creates a blood flow map m. The plurality of averaged blood flow maps n arranged along the time axis from the beginning of the heartbeat will be referred to as heartbeat maps. The heartbeat maps n created by the heartbeat map creation section 13 are sent to a combined map creation section 14 and a waveform numerical value creation section 15. In the combined map creation section 14, the heartbeat maps n created by the heartbeat map creation section 13 are averaged so as to create a single combined map (FIG. 20).

When the averaged blood flow values on the heartbeat maps are arranged in a chronological order, a blood flow change due to pulsations as shown in FIG. 19 is confirmed. FIG. 19 is a graph showing time-course changes in blood flow during a single heartbeat. The blood flow change is used as a base for calculation of the waveform numerical values. The waveform numerical value creation section 15 produces, from this blood flow change due to pulsation, a waveform numerical value which is obtained by digitizing the hemodynamics, such as the degree of distortion, within the region of interest. The waveform numerical value is sent to a waveform map creation section 16 and is also sent to a surface layer-background separation section 17 which will be described later. The waveform map creation section 16 creates a waveform map which includes the waveform numerical value superimposed on the image.

Unlike a quantitative index value representing the amount of blood flow, the waveform numerical value represents the resistance of the blood vessel from the arteriolar blood vessel to the peripheral blood vessel. The waveform numerical value is an index which allows comparison among individuals and allow comparison among individuals in terms of the state of blood flow (the quality of blood flow) which is represented by the blood vessel resistance. Also, it has been found that the waveform numerical value allows a determination as to whether the pulsation of a blood vessel is an arterial pulsation or a venous pulsation, and therefore the waveform numerical value is useful for distinguishing arteriovenous blood vessels within the map.

On the basis of the combined map created (FIG. 20), the surface layer-background separation section 17 calculates a numerical value of blood flow in the region of interest; for example, a histogram of blood flow values within the region of interest. From this histogram of the blood flow distribution, the surface layer-background separation section 17 determines a threshold of the blood flow value for separating the surface layer and the background region, and separates the surface layer and the background while using the threshold (reference) as a boundary. Further, the surface layer-background separation section 17 separates the surface layer blood flow and the background blood flow on the basis of the waveform numerical value, such as the degree of distortion, created by the waveform numerical value creation section 15. For example, in the case where a large blood vessel is present, peripheral blood vessels for nourishing the tissue are present around the large blood vessel, and these peripheral blood vessels are called "tissue blood vessels." Since the large blood vessel is present in the surface layer on the near side, the large blood vessel is called "surface layer blood flow. Since the tissue blood vessels extend deeper than the large blood vessel and include the background, the tissue blood vessels are called "background blood flow."

A separation map creation section 18 creates a separation map in which the surface layer and the background separated from each other are binarized. For example, the separation map creation section 18 creates a separation map in which a region of the separation map surface layer where the large blood vessel is present is colored white, and the region of the tissue blood flow present in the background is colored black. Since the separation map is a binary map in which, for example, the large blood vessel is colored white and the background blood flow is colored black, the separation map does not have information which allows comparison of their blood flow values as numerical values. The combined map created by the combined map creation section 14 is necessary for overview of the map and determination of the positions of blood vessels and is also necessary to know the blood flow values. Further, since the separation map is created, blood vessel system regions which differ in hemodynamics can be discriminated from each other by the separation map, whereby the display can be rendered easier to view.

In the case where the apparatus has succeeded in heartbeat detection, a combined map-additional information map superimposing section 19 superimposes, as upper layers, the waveform map created by the waveform map creation section 16 and the separation map created by the separation map creation section 18 on the lower layer; i.e., the combined map created by the combined map creation section 14. The display section 9 of FIG. 15 displays a map which is created by the combined map-additional information map superimposing section 19 in which the waveform map and the separation map of the region of interest coinciding with the distribution of blood flow of the combined map are superimposed. FIG. 21 exemplifiers a map which is displayed while being superimposed on the lower layer when the apparatus has succeeded in heartbeat detection. Within a circle p of FIG. 21, the separation map is displayed while being superimposed on the lower layer. A white region within the circle p represents the blood flow region of the surface layer, and a black region within the circle p represents the blood flow region of the background. Each of bar graphs q and r in FIG. 21 displays the degree of distortion (hereinafter referred to as the "Skew"), serving as a waveform numerical value, by graph display and also by a numerical value. The graph q represents the dynamics index Skew of the surface layer blood flow, and the graph r represents the dynamics index Skew of the background blood flow. The Skew is a numerical value obtained by multiplying the degree of distortion (skewness) by a constant.

As described above, the heartbeat analysis section 12 analyses the blood flow maps from the blood flow analysis section 11, and searches a blood flow map whose blood flow value is the lowest, thereby determining the lowest blood flow map for each heartbeat. However, in the case where the heartbeat analysis section 12 fails to determine the lowest blood flow map, all the blood flow maps stored chronologically are sent to the combined map creation section 14.

FIG. 22 is a pair of charts used for describing a case where the heartbeat detection was not performed successfully. FIG. 22 exemplifies blood flow values during a measurement period of 4 sec as time-course changes S of blood flow. The blood flow values shown in FIG. 22 do not involve large pulsations. The combined map creation section 14 averages the plurality of time-series blood flow maps t (the first map u to the last map v) created by the blood flow analysis section 11, to thereby create a single blood flow map shown in FIG. 23. This will be referred to as a combined map. The blood flow map obtained through the first measurement started at an arbitrary time is the first map (leading map), and the blood flow map obtained through the last measurement ended after elapse of a predetermined time after the first measurement is the last map. Irrespective of whether or not the first map is obtained in the middle of a pulsation, all the maps (from the first map to the last map) are averaged.

In the case where the heartbeat detection was not performed successfully, the surface layer-background separation section 17 cannot utilizes the waveform numerical values. However, the surface layer-background separation section 17 can obtain a histogram on the basis of the blood flow values within the region of interest on the combined map and can separate the surface layer and the background from this distribution. Therefore, the separation map can be created from the combined map only. FIG. 24 exemplifies a map which is displayed while being superimposed on the lower layer in the case where the heartbeat detection was not performed successfully. In the drawing, numerical values such as waveform numerical values are not displayed.

In the case where the apparatus failed to detect heartbeats, only the combined map and the separation map are created and are superimposed by the combined map-additional information map superimposing section 19. Only a map from which a region where the blood flow is fast and a region where the blood flow is slow can be visually recognized can be provided to the display section 9. For data from which heartbeats cannot be detected, a map in which hemodynamics are indexed cannot be created, and a dynamics index cannot be expressed on the map. A plurality of blood flow maps which change with pulsations can be observed. However, they do not have objective indexes, comparison among individuals cannot be performed through use of the maps as they are. Since pulsations are not remarkable at peripheral tissues such as skin, the conventional apparatus is likely to fail to detect heartbeats and cannot create a waveform map. Therefore, in some cases, comparison of hemodynamics was impossible. Since the waveform numerical value is not a dynamics index focused on the intensity of the frequency of pulsation, the comparison of the strength of pulsation was impossible for the case of a mild blood flow change in which a blood flow variation due to pulsations is small.

Since the combined map itself does not contain information of time-course changes, a separation map created on the basis of the combined map only cannot express information of the strength of pulsation, etc. Also, the waveform map having temporal information requires the heartbeat detection by the heartbeat analysis section 12. Therefore, the waveform map which expresses the hemodynamic index cannot be obtained from data for which the heartbeat detection fails. As described above, in the case of the conventional technique, when the heartbeat detection fails, only the averaged blood flow value is obtained as the information regarding hemodynamics, the information regarding the dynamics such as the quality of blood flow is lost. Therefore, it was not that sufficient functions are provided for all the data obtained through measurement of blood flow.

PRIOR ART DOCUMENTS

Patent Documents

Patent Document 1: Japanese Patent Publication (kokoku) No. H5-28133
Patent Document 2: Japanese Patent Publication (kokoku) No. H5-28134
Patent Document 3: Japanese Patent Application Laid-Open (kokai) No. H4-242628
Patent Document 4: Japanese Patent Application Laid-Open (kokai) No. H8-112262
Patent Document 5: Japanese Patent Application Laid-Open (kokai) No. 2003-164431
Patent Document 6: Japanese Patent Application Laid-Open (kokai) No. 2003-180641
Patent Document 7: WO 2014/175154
Patent Document 8: WO 2008/69062

SUMMARY OF THE INVENTION

Problems to be Solved by the Invention

In the case of a patient suffering from diabetes, when the pathological condition becomes severe, the patient suffers from foot disease, and his/her toe necrotizes. In such a case, pulsation partially becomes unstable in a specific portion of the toe, and differs from the healthy portion of the toe in terms of hemodynamics. The result of discrimination between the healthy portion of the toe and the portion whose necrosis has started and which has no pulsation may be an important piece of information for the patient and the doctor who want to keep the healthy region without cutting. Therefore, an apparatus for imaging and analyzing hemodynamics which can perform non-contact two-dimensional measurement in a simple and easy manner has been demanded.

The conventional diagnosis equipment which has been described with reference to FIGS. 15 and 16 utilizes the periodical pulsation of blood flow and requires a process called "heartbeat analysis" which is performed on the basis of successive time-series blood flow maps. In the case where heartbeat detection is possible, a blood flow waveform is extracted from the heartbeat map, hemodynamics such as the degree of distortion within the region of interest are digitized as the waveform numerical value and are mapped, whereby information beneficial to clinical analysis can be provided.

However, in the case where heartbeat detection is impossible, a single averaged blood flow map in which pulsation is ignored is created from time-series blood flow maps, and is visualized as a map. It has been only possible to visualize a region where blood flow is fast and a region where blood flow is slow and compare the averaged blood flow values within the region of interest.

At a location where inflammation has occurred, a larger blood flow as compared with that in the ordinary state is observed. However, it has been impossible, through mere observation of the combined map, to know the blood vessel resistance produced in a portion of the observed region and the restricted flow in that portion. Conventionally, only the data from which heartbeats have been extracted successfully can output the waveform numerical value, and the waveform numerical value cannot be applied to all the blood flow data.

In particular, in the case of the skin blood flow, although the amount of blood flow is relatively large, the regular blood flow change which occurs in synchronism with heartbeats is small, because the skin blood flow is the blood flow on the peripheral side. This phenomenon becomes remarkable toward the peripheral side, and it becomes very difficult to find a periodic blood flow change which appears to be pulsation. Also, the peripheral blood flow involves a slower bool flow change which occurs asynchronous with pulsation, there have been many cases where the heartbeat extraction process fails, and the calculation of the waveform numerical value and the creation of the heartbeat map are impossible. As described above, the conventional heartbeat analyzing method cannot be applied to all the blood flow data obtained through measurement, and there has been a limit on the indexing of the skin hemodynamics.

In view of the above, an object of the present invention is to allow a heartbeat strength which represents the strength of pulsation (beat) to be imaged on a map as a new dynamics index different from the conventional waveform numerical value, to thereby allow comparison of difference in hemodynamics not only among individuals but also among regions within the map. Thus, it becomes possible to obtain the heartbeat strength which is an objective numerical index of hemodynamics for all data sets including a data set for which heartbeat detection fails.

Means for Solving the Problems

An apparatus and a method for imaging and analyzing hemodynamics according to the present invention comprises a laser light irradiation system for applying laser light to an observation area of a biotissue including blood cells; a light receiving section composed of a plurality of pixels for detecting reflection light from the observation area of the biotissue; an image capturing section for successively capturing a plurality of images on the basis of a signal from the light receiving section; an image storage section for storing the plurality of images; a computation section for computing a blood flow speed within the biotissue from time-course changes of output signals of corresponding pixels of the plurality of images stored; and a display section for displaying, as a blood flow map, a two-dimensional distribution which is the result of the computation.

The computation section obtains, from a time-course change of the blood flow map obtained as a result of the computation of the blood flow speed, a signal intensity at a fundamental frequency determined from time-series blood flow data within a predetermined region, and calculates a heartbeat strength which represents the strength of heartbeats on the basis of the signal intensity. The display section images and displays the heartbeat strength calculated by the heartbeat strength computation section.

Also, the display section displays the heartbeat strength calculated by the heartbeat strength computation section by superimposing the heartbeat strength on a combined map created by averaging a plurality of blood flow maps arranged in a chronological order. Also, the display section images and displays a frequency corresponding to the heartbeat strength together with the heartbeat strength. The frequency may be displayed as a numerical value obtained by converting the frequency to a heart rate.

Also, the display section can display a waveform map which represents a waveform numerical value obtained by digitizing hemodynamics caused by changes in blood flow, or a separation map created on the basis of surface layer-background separation information. Also, the display section can visually expresses the magnitude of the heartbeat strength or the frequency near the display of the predetermined region.

The heartbeat strength computation section comprises a blood flow power spectrum model analysis section which uses the time-series blood flow data of the predetermined region, transforms the time-course changes of the blood flow into a frequency domain through Fourier series expansion, predicts a power spectrum on the basis of the blood flow data transformed into the frequency domain, determines, as the fundamental frequency, a frequency at which power becomes maximum within the distribution of the predicted power spectrum, obtains a signal intensity corresponding thereto, and calculates the heartbeat strength; and a heartbeat strength map creation section which images the heartbeat strength which distributes two-dimensionally. Also, the blood flow power spectrum model analysis section obtains one or more signal intensities corresponding to one, two or more frequency ranges previously set within the distribution of the predicted power spectrum, and calculates the heartbeat strength. The combined map can be created by averaging all the plurality of blood flow maps arranged in the chronological order or is created by creating heartbeat maps by averaging corresponding blood flow maps in one, two, or more pulsations, while using, as a reference, a leading map determined for the one, two, or more pulsations, and by averaging the heartbeat maps.

The predetermined region for which the time-series blood flow data are obtained is a region which an observer is interested in, which is set on the blood flow map, and whose shape is arbitrarily determined by the observer, or the entire blood flow map, or a region obtained by dividing the blood flow map.

Effects of the Invention

Conventionally, since heartbeats cannot be detected from the mild fluctuation of blood flow whose change due to pulsations is small, an objective numerical index of hemodynamics cannot be obtained. In contrast, according to the present invention, even in the case of the blood flow fluctuation for which heartbeat detection fails, the heartbeat strength which serves as an objective numerical index of hemodynamics can be obtained for all data.

Also, according to the present invention, for all blood flow data, the hemodynamic index is digitized and displayed without heartbeat extraction processing. Therefore, the present invention has an advantageous effect that the difference in hemodynamics not only between individuals but also between different regions within the map can be determined and analyzed by quantitatively and visually comparing their hemodynamics.

Conventionally, in the case where heartbeats can be detected successfully, a waveform numerical value which represents hemodynamics such as the degree of distortion by a numerical value can be obtained. The degree of distortion is a numerical value for distinguishing a portion which has an arterial waveform involving steep risings and a portion which has a venous waveform involving mild fluctuations. However, since the detection of heartbeats may fail on the peripheral side, the chance of success in obtaining such a waveform numerical value is unstable. In contrast, the heartbeat strength which represents the strength of heartbeats can express the hemodynamics without fail at any location.

BRIEF DESCRIPTION OF THE DRAWINGS

FIG. 7 is an example of a feasible code for solving the minimization problem of the LASSO method.

MODES FOR CARRYING OUT THE INVENTION

Figure 1:
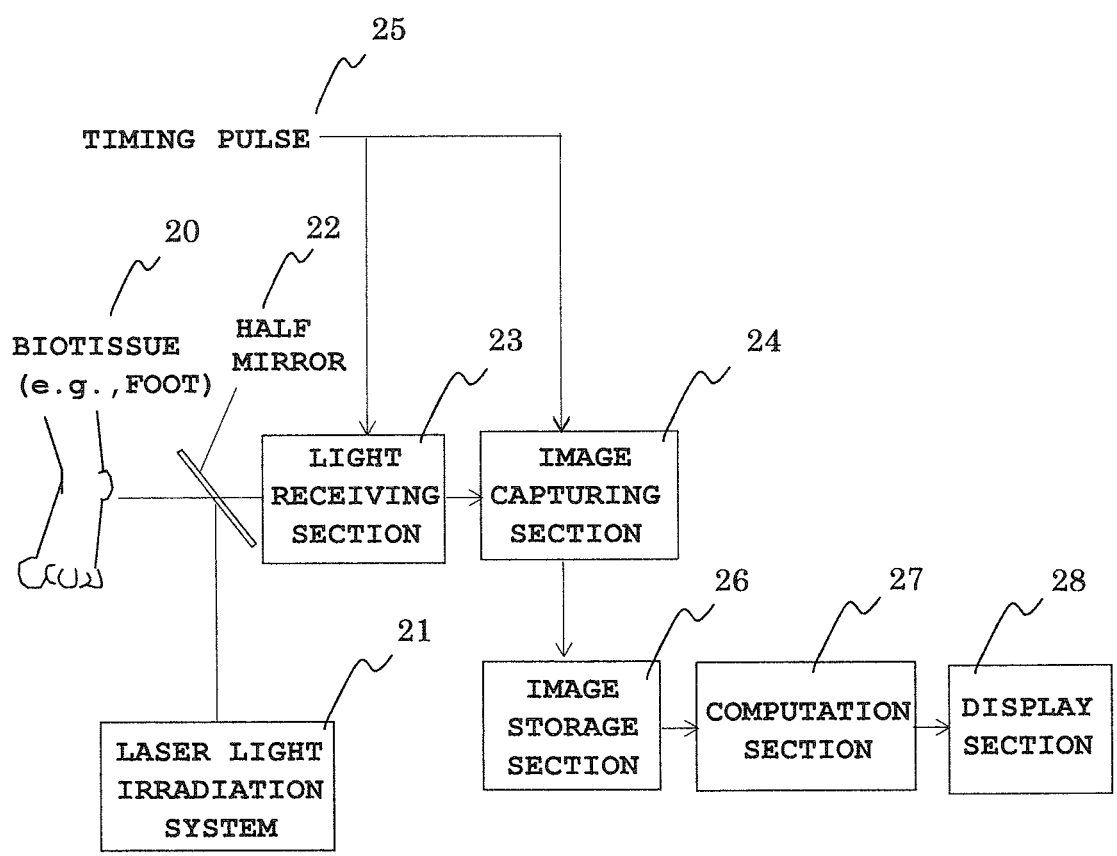
FIG. 1 shows an example of a schematic overall configurational diagram of a hemodynamics imaging and analyzing apparatus configured on the basis of the present invention.

Now, the present invention will be described on the basis of an example. FIG. 1 shows an example of a schematic overall configurational diagram of a hemodynamics imaging and analyzing apparatus configured on the basis of the present invention. A laser light irradiation system 21 applies laser light, through a half mirror 22, to a biotissue 20 (e.g., dorsum of foot) having blood flows such as skin blood flow, internal organ blood flow, and eyeground blood flow. A light receiving section 23 includes a solid state imaging device (e.g., CCD, CMOS, etc.) having a large number of pixels on its light receiving surface, a light receiving lens which focuses laser reflection light on the solid state imaging device, an amplification circuit for amplifying the output of imaging elements, etc. The solid state imaging device may use imaging elements disposed two-dimensionally or imaging elements disposed one-dimensionally. The imaging elements driven on the basis of timing pulses 25 convert an image of the biotissue formed by the light receiving lens to an electric signal on the basis of the timing pulses 25. The solid state imaging device reads out signal charges in a frame storage mode, and amplifies and outputs them as an image signal.

Analog processing such as gain control is performed on the output image signal, and a resultant analog signal is converted to a digital signal. On the basis of this digital signal and the timing pulses, an image capturing section 24 successively captures a plurality of images at predetermined intervals (e.g., intervals of 1/30 sec) equal to or greater than one or two heartbeats. An image storage section 26 stores data of the captured images. A computation section 27 computes the blood flow speed within the biotissue from the time-course changes of output signals of corresponding pixels throughout the plurality of stored images. The configuration of the above-described hemodynamics imaging and analyzing apparatus may be rendered identical to the conventional configuration (see Patent Document 8) described with reference to FIG. 1 except for the configuration of the computation section 27.

From the time-course changes of a blood flow map obtained through computation, the computation section 27 of the present invention calculates a heartbeat strength which represents the strength of heartbeat within at least one region of interest on the blood flow map. Also, the computation section 27 can output a frequency corresponding to the heartbeat strength along with the heartbeat strength. A display section 28 displays blood flow map information and superimposes heartbeat strength information thereon. In addition, as in the case of the conventional technique, the computation section 27 can superimpose information (e.g., a waveform map representing waveform numerical values and a separation map created on the basis of surface layer/background separation information) useful for diagnosis on the blood flow map and can display the maps as two-dimensional distribution information. The details of the configuration of the computation section 27 of the present invention will be described with reference to FIG. 2.

Figure 2:
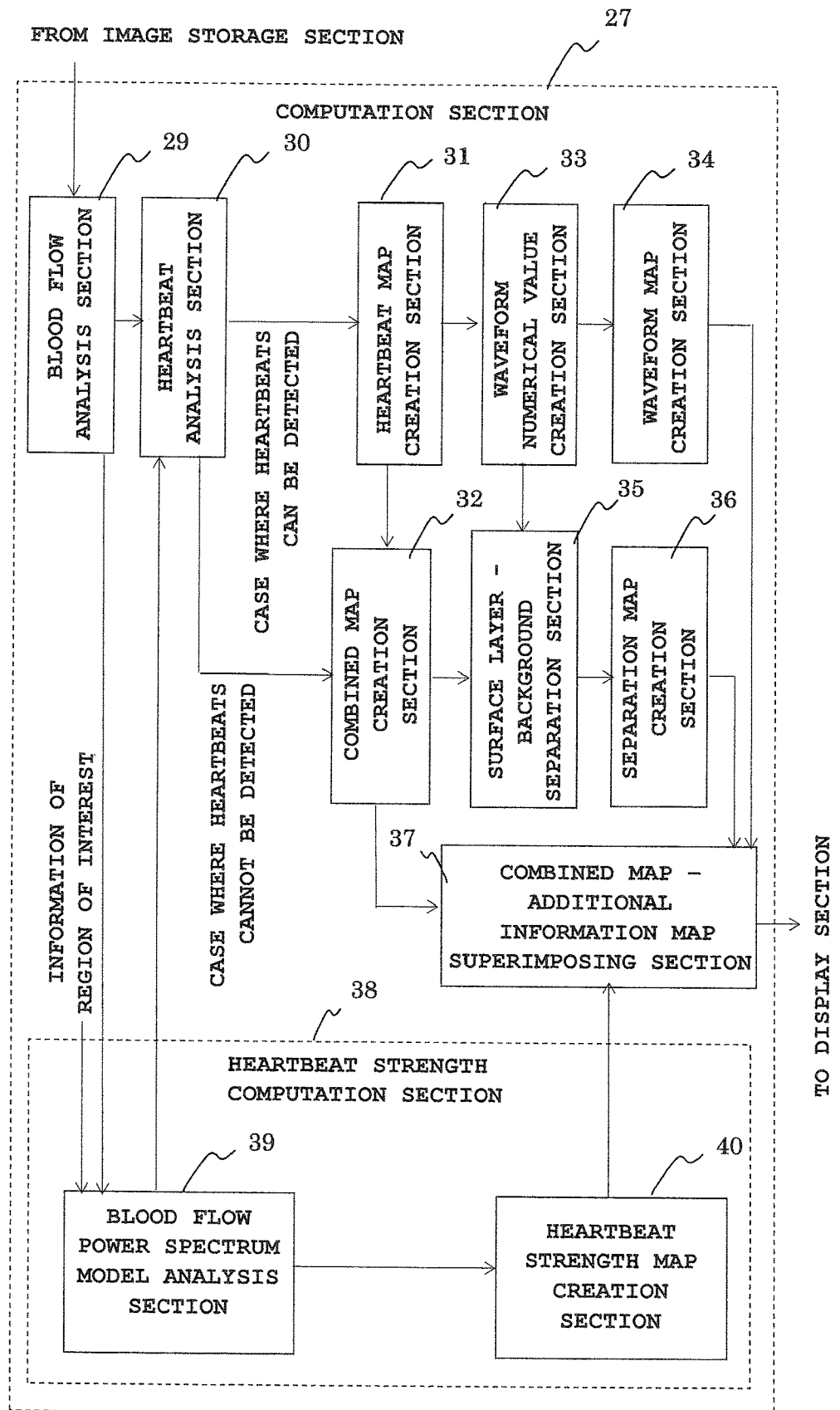
FIG. 2 shows an example of a configurational diagram of a computation section which is the feature of the present invention.
Figure 16:
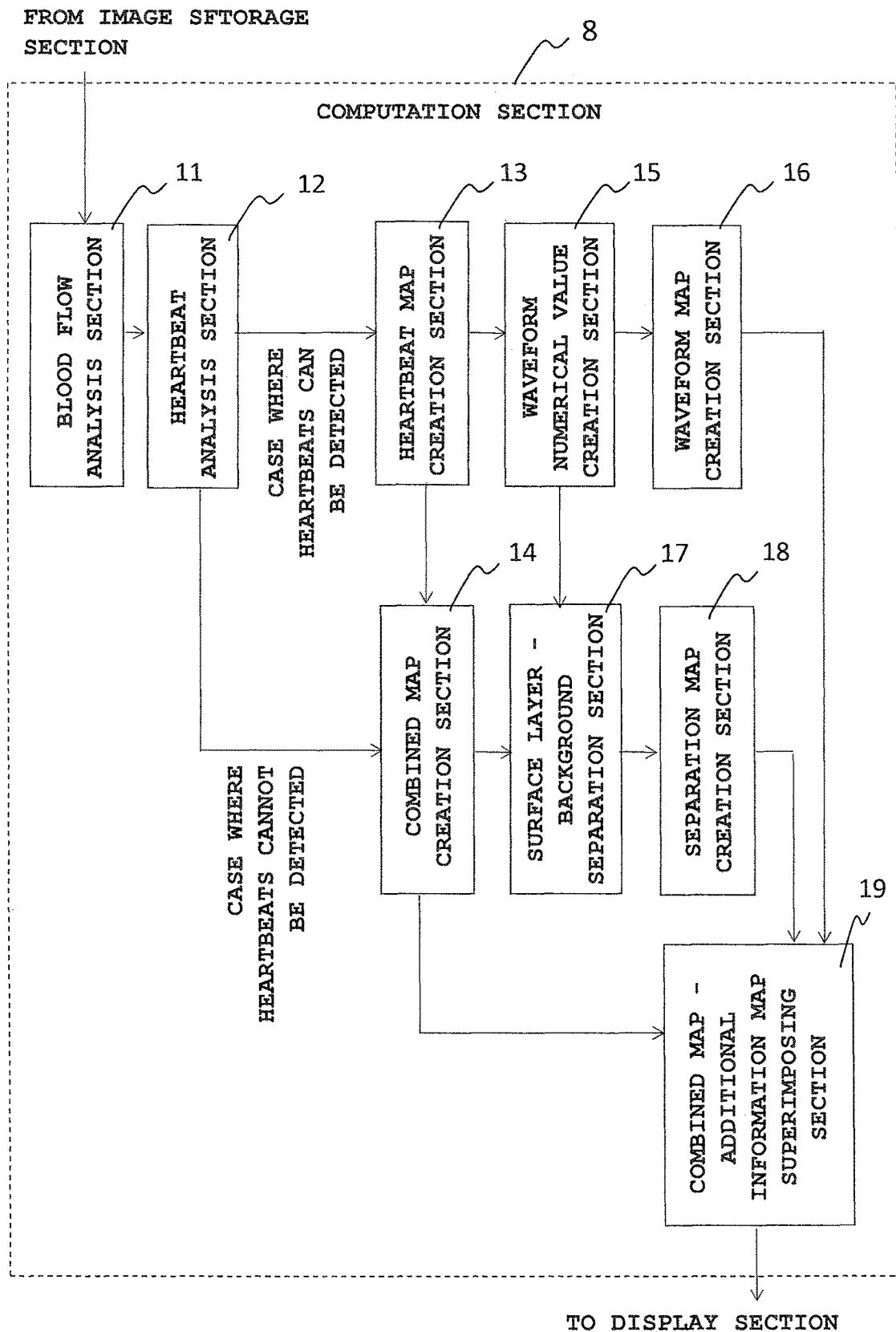
FIG. 16 shows an example of a computation section of the hemodynamics imaging and analyzing apparatus according to the conventional technique.
Figure 17:
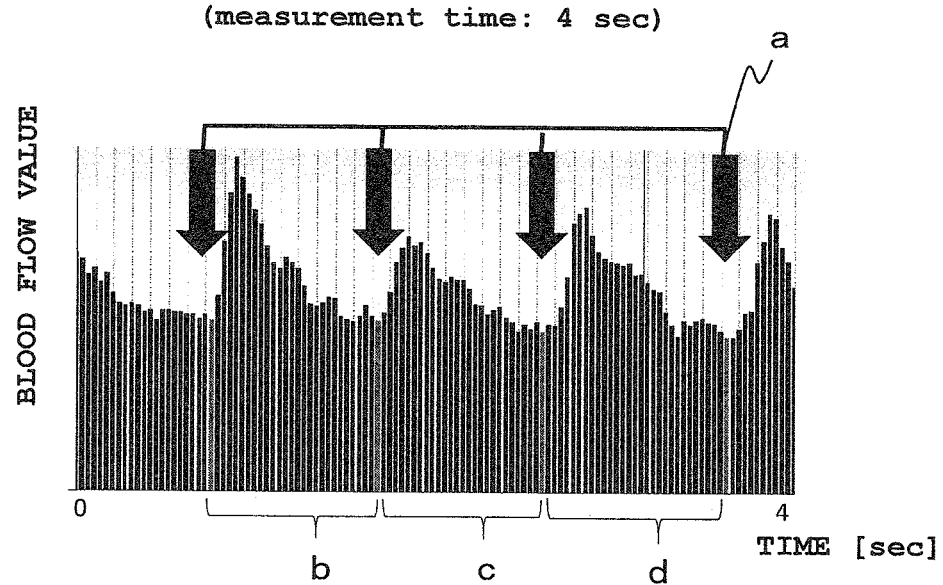
FIG. 17 shows time-course changes of blood flow for the case where heartbeats have been detected successfully.
Figure 18:
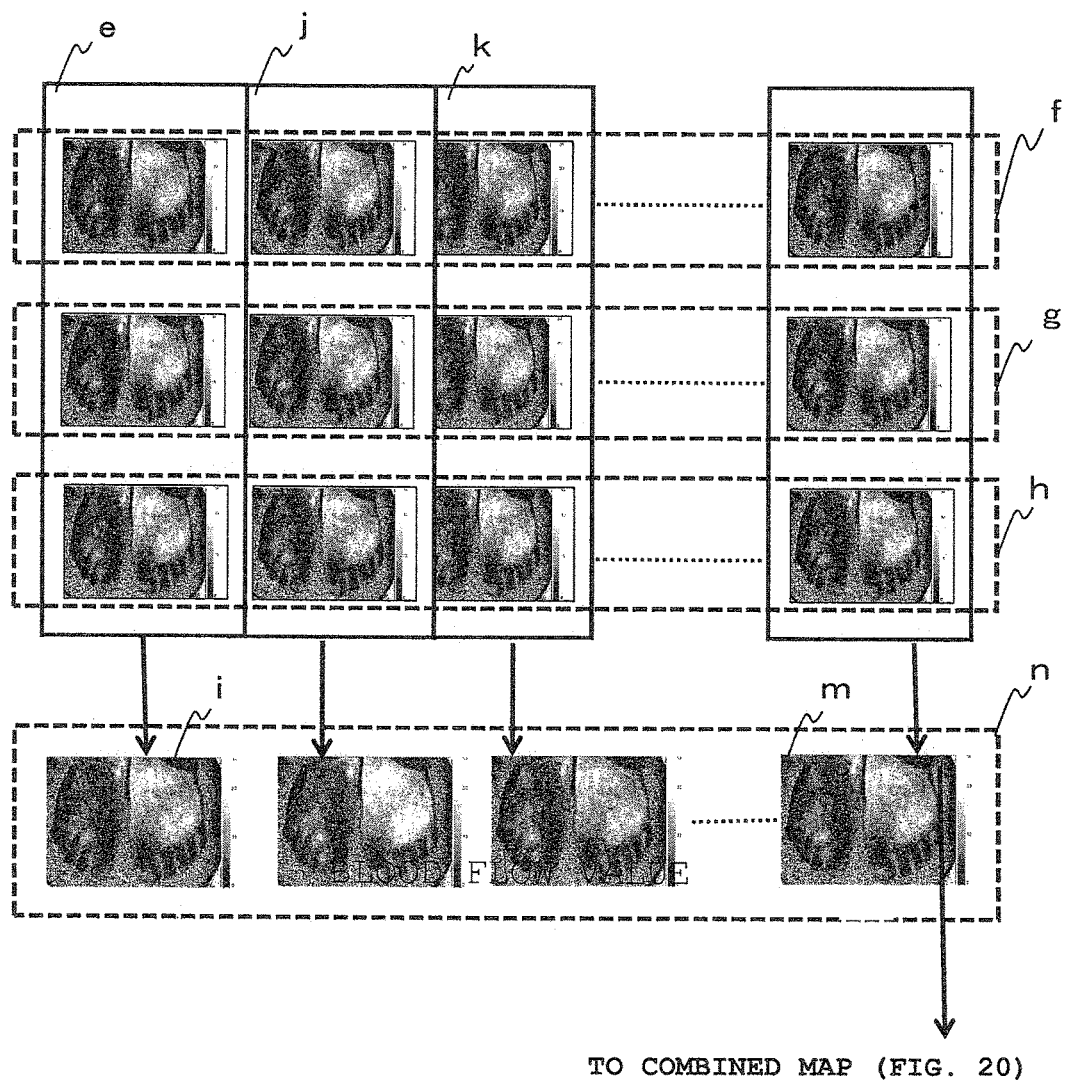
FIG. 18 is an illustration used for describing a method for creating a combined map from a plurality of blood flow maps corresponding to pulsations.
Figure 19:
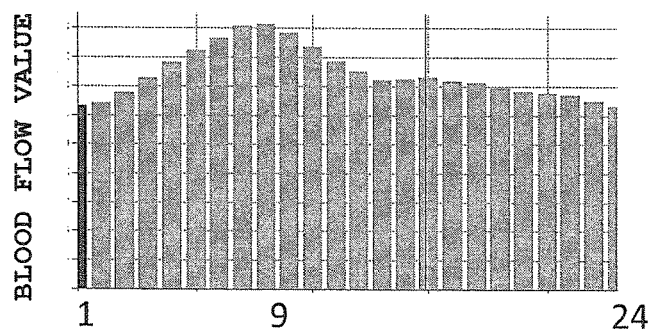
FIG. 19 is a graph showing time-course changes of blood flow during a single heartbeat.
Figure 20:
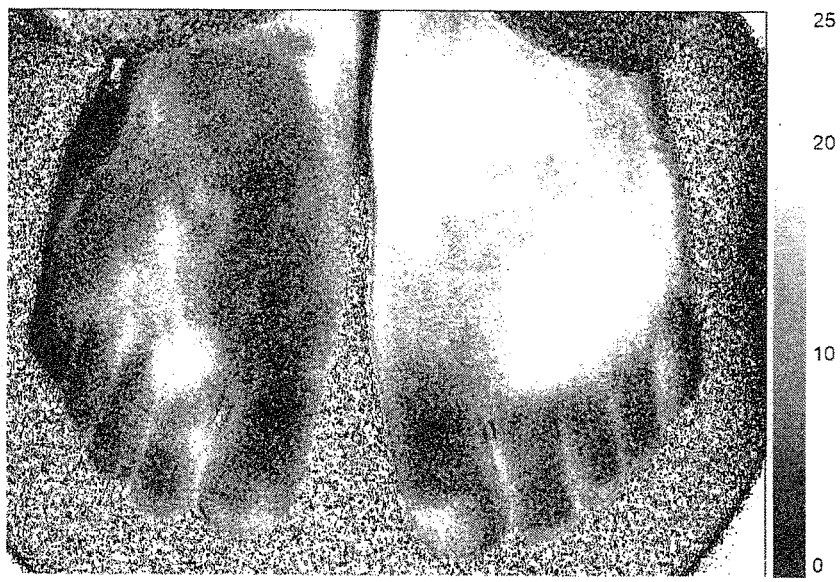
FIG. 20 exemplifies a combined map created in the case where heartbeats have been detected successfully.

FIG. 2 is a configurational diagram exemplifying the computation section 27 which is the feature of the present invention. A heartbeat strength computation section 38 composed of a blood flow power spectrum model analysis section 39 and a heartbeat strength map creation section 40 is provided in the computation section 27. Blood flow map information from a blood flow analysis section 29 is input to the blood flow power spectrum model analysis section 39 together with region-of-interest information. An output signal of the blood flow power spectrum model analysis section 39 is input to the heartbeat analysis section 30, and an output signal of the heartbeat strength map creation section 40 is input to a combined map-additional information map superimposing section 37. The computation section 27 is identical with the conventional computation section (conventional technique) having been described with reference to FIG. 16 except for the above-described points and operates in the same manner as the conventional computation section. The detailed description of the identical portion will not be repeated.

Figure 4:
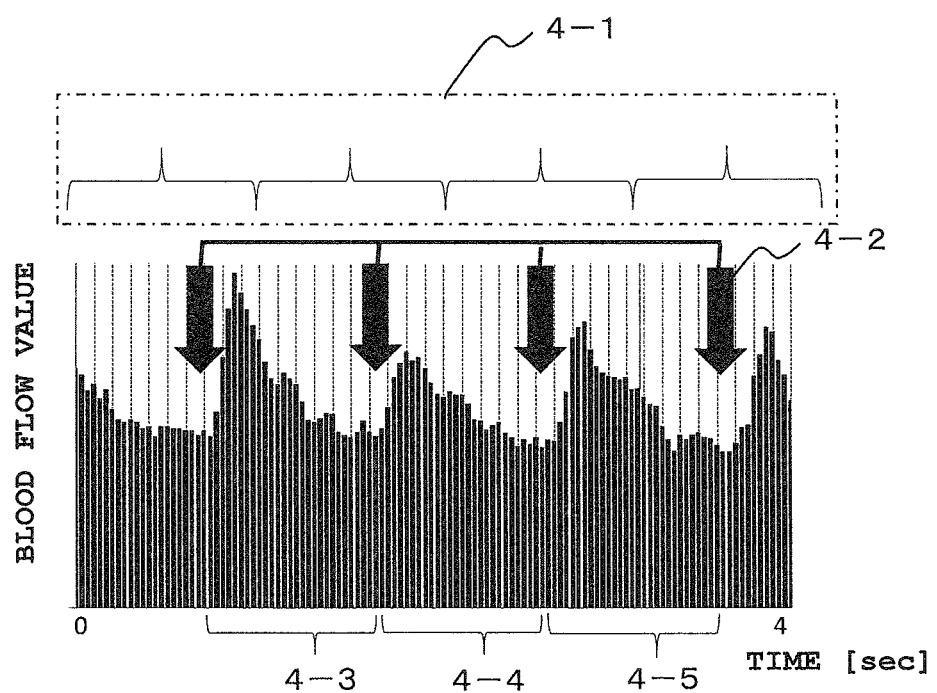
FIG. 4 is a chart exemplifying time-course changes of blood flow.

The blood flow analysis section 29 analyzes the images fetched from the image storage section 26 and creates a blood flow map in which the blood flow in the biotissue is displayed by a two-dimensional image. The blood flow analysis section 29 calculates the blood flow speed in the organism from time-course changes of the output signals of corresponding pixels of the plurality of stored images. In FIG. 4, this computed blood flow value is shown as time-course changes of blood flow. In general, the blood flow value pulsates. Each of (four) arrows 4-2 on the upper side of FIG. 4 shows the temporal position of a lowest blood flow map in each pulsation.

As in the above-described conventional technique, the heartbeat analysis section 30 obtains, from the means for searching the lowest blood flow map for each pulsation, the number of maps per heartbeat. In addition, the heartbeat analysis section 30 obtains the number of maps per heartbeat on the basis of the frequency corresponding to the heartbeat strength obtained by the blood flow power spectrum model analysis section 39. The heartbeat analysis section 30 compares the numbers of maps per heartbeat obtained by these two methods, and determines an optimal map number per heartbeat. By this method, the probability of success of heartbeat detection increases as compared with the conventional technique. Subsequently, as shown in FIG. 4, the time-series blood flow maps obtained by the blood flow analysis section 29 are divided (4-1), from the beginning, into groups whose map number is equal to the determined map number per heartbeat, and the lowest blood flow map in each pulsation is searched. In the case shown in FIG. 4, blood flow map groups 4-3, 4-4, 4-5, etc. which correspond to respective pulsations are obtained.

The heartbeat analysis section 30 determines that the obtained lowest blood flow map in each heartbeat is to be used as the leading map (first map) and that heartbeats have been detected successfully. Subsequently, a heartbeat map creation section 31 operates. The processes performed in the heartbeat analysis section 30 and sections subsequent thereto are the same as those in the conventional technique. In short, in the case where the blood flow maps during two or more pulsations are used, the heartbeat map creation section 31 uses the determined leading map as a reference and averages the corresponding blood flow maps to thereby create a blood flow map. A heartbeat map can be created from the blood flow maps during a single pulsation. However, in this case, the averaging process is not needed. The plurality of averaged blood flow maps arranged along the time axis will be referred to as heartbeat maps. In a combined map creation section 32, the heartbeat maps created by the heartbeat map creation section 31 are averaged so as to create a single combined map.

When the averaged blood flow values on the heartbeat maps are arranged in a chronological order, a blood flow change due to pulsations can be confirmed. This blood flow change is used as a base for calculation of the waveform numerical values. As in the case of the conventional technique, a waveform numerical value creation section 33 can produce, from this blood flow change due to pulsation, a waveform numerical value which represents, by a numerical value, hemodynamics, such as the degree of distortion, within the region of interest. A waveform map creation section 34 can create a waveform map in which the waveform numerical value created by the waveform numerical value creation section 33 is superimposed on the image.

On the basis of the combined map created, a surface layer-background separation section 35 separates the surface layer and the background while using the threshold (reference) as a boundary. As in the case of the conventional technique, a separation map creation section 36 creates a separation map in which the surface layer and the background separated from each other are binarized, whereby the display can be rendered easier to view. Also, the separation information pieces of the surface layer and the background separated from each other may be re-defined as a region of interest of the blood flow region of the surface layer and a region of interest of the background blood flow and may be used as information input to the blood flow power spectrum model analysis section 39.

In the case where the heartbeat analysis section 30 fails to determine the lowest blood flow map; i.e., fails to perform the heartbeat detection successfully, all the blood flow maps stored chronologically are sent to the combined map creation section 32. The combined map creation section 32 averages the plurality of time-series blood flow maps (the first map to the last map) created by the blood flow analysis section 29, to thereby create a single blood flow map. This will be referred to as a combined map.

In the case where the heartbeat detection was not performed successfully, the surface layer-background separation section 35 cannot utilizes the waveform numerical value created by the waveform numerical value creation section 33. However, the surface layer-background separation section 35 can obtain a histogram on the basis of the blood flow values within the region of interest on the combined map and can separate the surface layer and the background from this distribution. Therefore, the separation map can be created from the combined map only. As described above, in the case where the heartbeat detection fails, only the combined map and the separation map are created and superimposed at the combined map-additional information map superimposing section 37.

Notably, as described above, in the case where the heartbeat maps are created, the combined map can be created by averaging the heartbeat maps, and in the case where the heartbeat maps are not created, the combined map can be created by averaging all the plurality of blood flow maps arranged in the chronological order. However, in order to create the waveform numerical values to be displayed on the waveform map, the heartbeat maps must be created. Also, in order to perform more accurate separation at the surface layer-background separation section 35, creation of the heartbeat maps is desired.

Next, the heartbeat strength computation section 38 which is the feature of the present invention will be described. The blood flow analysis section 29 obtains and analyzes the time-course changes of the output signals of corresponding pixels of the plurality of images stored in the image storage section 26. A plurality of blood flow maps in the chronological order are output, as the result of the analysis, not only to the heartbeat analysis section 30 but also to the blood flow power spectrum model analysis section 39.

The blood flow power spectrum model analysis section 39 creates time-series blood flow data by averaging the blood flow values on the blood flow maps in the chronological order for each region of interest. The region of interest is one region or each of two or more regions in which an observer has an interest and which has an arbitrarily set shape such as a rectangular shape, an oval shape, a polygonal shape, a grid-like shape. In some cases, the region of interest may be the entire blood flow map or each of regions obtained by appropriately dividing a map obtained through image processing of the blood flow maps analyzed by the blood flow analysis section 29 such that the regions have arbitrary shapes.

For each region of interest, the blood flow power spectrum model analysis section 39 receives the time-series blood flow data as an input and outputs a heartbeat strength representing the strength of heartbeat and a frequency corresponding to the heartbeat strength. The time-series blood flow data may be obtained by extracting a certain number (e.g., about 1,000) samples from the blood flow values present in the region of interest and performing an arithmetic operation such as averaging on the extracted blood flow values. Also, the time-series blood flow data may be obtained by a method which employs an elapsed time of each heartbeat at which the blood flow value becomes maximum.

The heartbeat strength is obtained as follows. A power spectrum which is the frequency distribution of intensity is obtained from the time-series blood flow data, and the feature of the obtained power spectrum; i.e., an undulating shape representing the amplitude of power, is obtained. The heartbeat strength is determined on the basis of the undulating shape. For example, a frequency at which the power becomes maximum in the power spectrum distribution is determined, and a numerical value obtained by multiplying the power corresponding to the frequency by a constant is used as the heartbeat strength. Thus, the heartbeat strength is used as a hemodynamic index which can be compared together with the frequency corresponding to the heartbeat strength.

In the result of Fourier expansion of the time-series blood flow data, the amplitude of the first fundamental wave corresponds to the heartbeat strength, and the frequency of the first fundamental wave (fundamental frequency) corresponds to the frequency having the heartbeat strength. In the present invention, the coefficients of the Fourier series which is obtained as a result of Fourier expansion necessary for calculation of the heartbeat strength are predicted. The term "prediction" means a process in which a power spectrum which cannot be obtained unless a very long time-series blood flow data set is obtained is predicted in advance through use of a limited short time-series blood flow data set.

Figure 5:
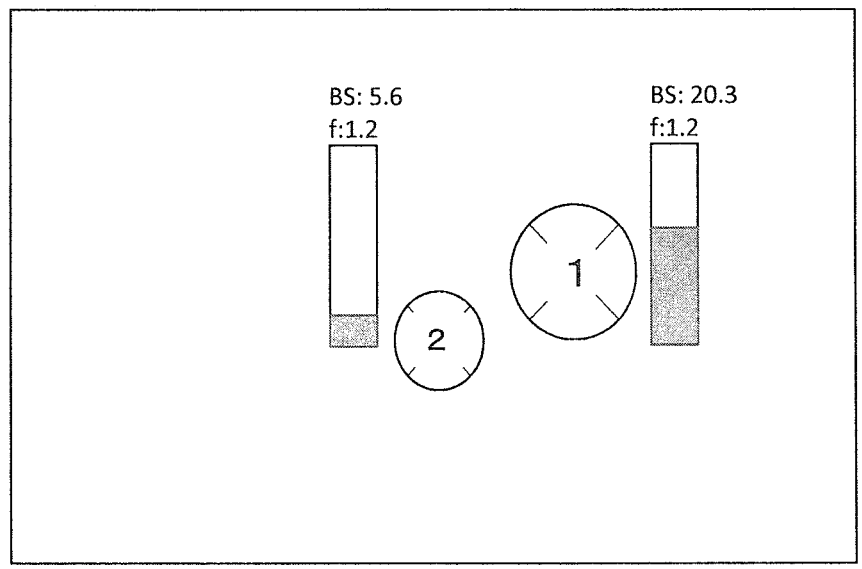
FIG. 5 is an example of a created heartbeat strength map.

The heartbeat strength map creation section 40 creates, for each region of interest, a heartbeat strength map in which the strength of pulsation is mapped. FIG. 5 is an illustration shows the heartbeat strength map solely. In this example, bar graphs are provided near a plurality of regions of interest 1 and 2 (two circles) so as to show the magnitudes of heartbeat strengths by visual representation.

A numerical value obtained by converting the frequency to the heart rate can be displayed as the frequency corresponding to the heartbeat strength. In the case where the numerical value obtained by the conversion is close to the heart rate, an observer can determine whether it represents beats due to pulsations or a blood flow variation relating to the sympathetic nerve system or the parasympathetic nerve system, which variation is often observed in the peripheral blood flow. Therefore, it is useful for grasping the hemodynamics of the region of interest and is useful for clinical diagnosis.

Figure 6:
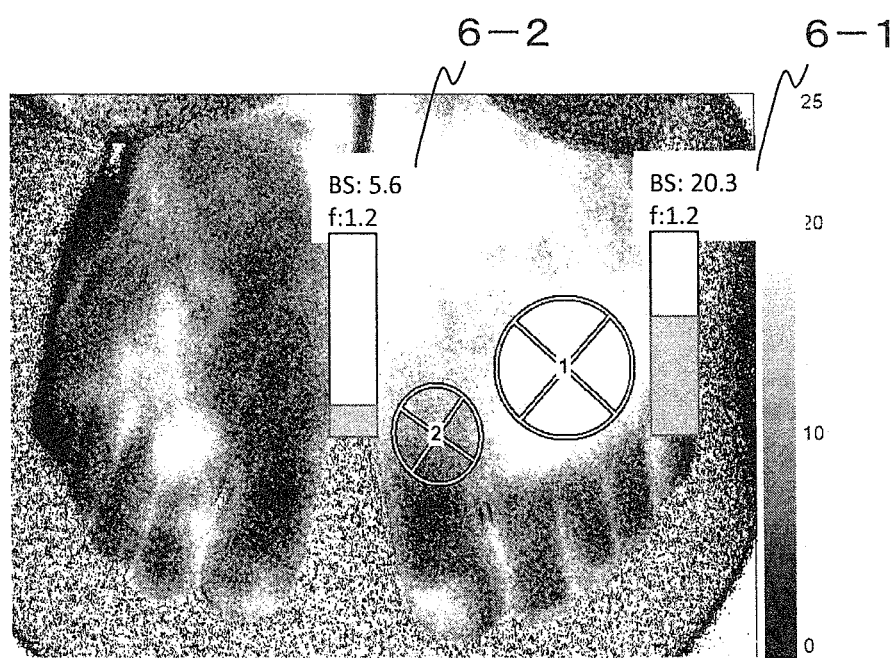
FIG. 6 is an example of display in which a combined map and the heartbeat strength map are superimposed.

In the combined map-additional information map superimposing section 37, the combined map created by the combined map creation section 32 is used as a lower layer, the heartbeat strength map (FIG. 5) which is created by the heartbeat strength map creation section 40 and in which the strength of pulsation is mapped in each region of interest is used as an upper layer, and these maps are superimposed as shown in FIG. 6.

As shown in FIG. 6, bar graphs are provided near the regions of interest 1 and 2 so as to show the magnitudes of heartbeat strengths by visual representation. Also, as indicated by 6-1 and 6-2 in FIG. 6, the heartbeat strength is displayed by a numerical value in the upper row, and the frequency is displayed by a numerical value in the lower row. Each bar graph may be colored in accordance with the magnitude of the numeral value to be displayed such that when the numerical value is large, the graph has a warm color such as red and when the numerical value is small, the graph has a cold color such as blue. The heartbeat strength or the frequency corresponding to the heartbeat strength may be depicted through use of other effective graphs, numerical representations, etc. Also, it is possible to store in the apparatus a numerical value representing the heartbeat strength at the time of the previous measurement and to depict a graph which allows comparison between the last value and the current value.

Thus, the combined map-additional information map superimposing section 37 creates a single map in which the distribution of pulsation strength (heartbeat strength) of the region of interest is disposed to coincide with the region of interest of the combined map and displays the single map at the display section 28 of FIG. 1. The display section 28 may display the combined map and the heartbeat strength map as different maps without superimposing them. Also, additional image process may be performed or additional information may be depicted on the maps for highlighted display of these maps.

Figure 21:
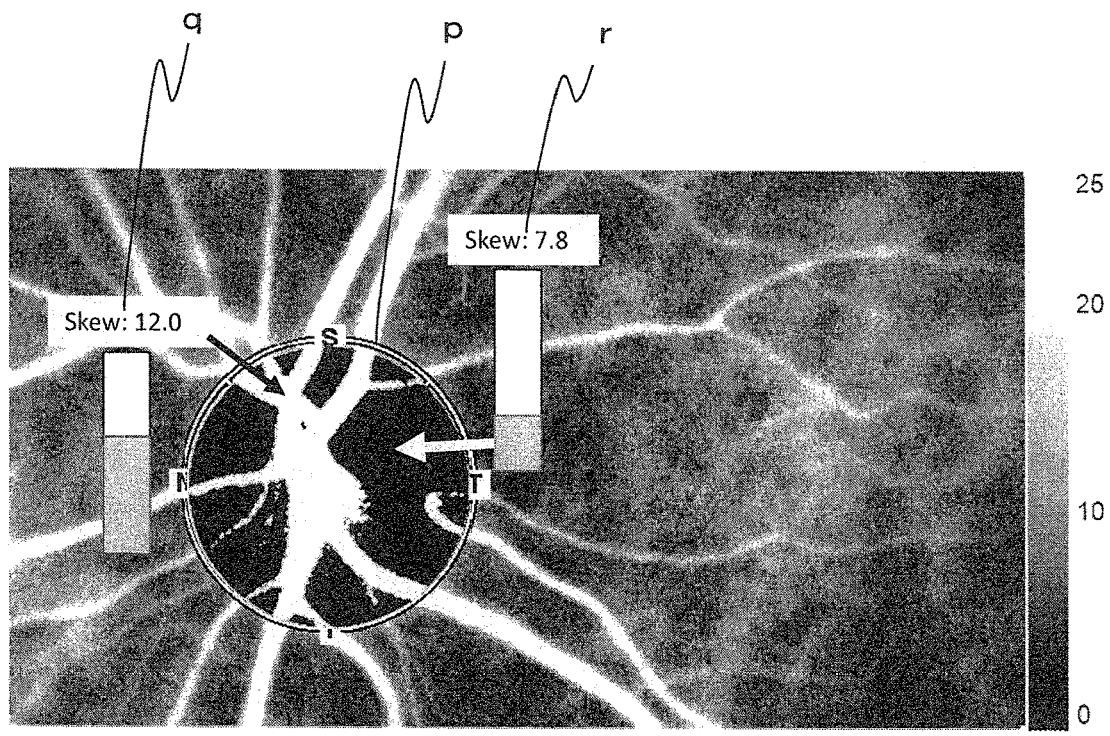
FIG. 21 shows an example in which a separation map and a waveform map are superimposed on the combined map.
Figure 22:
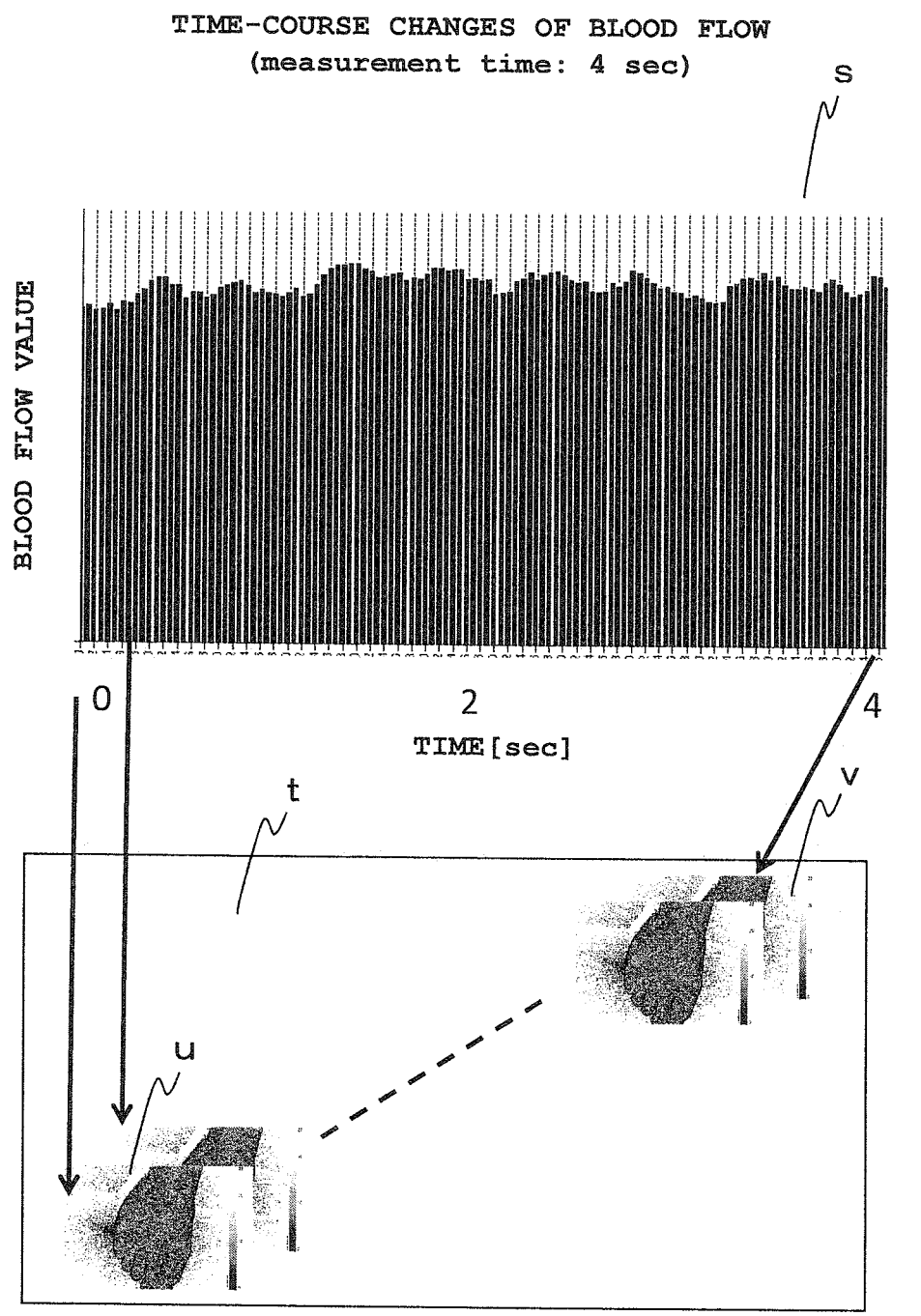
FIG. 22 is a pair of charts used for explaining the case where heartbeat detection was not performed successfully.
Figure 23:
FIG. 23 exemplifies a combined map created in the case where heartbeat detection was not performed successfully.
Figure 24:
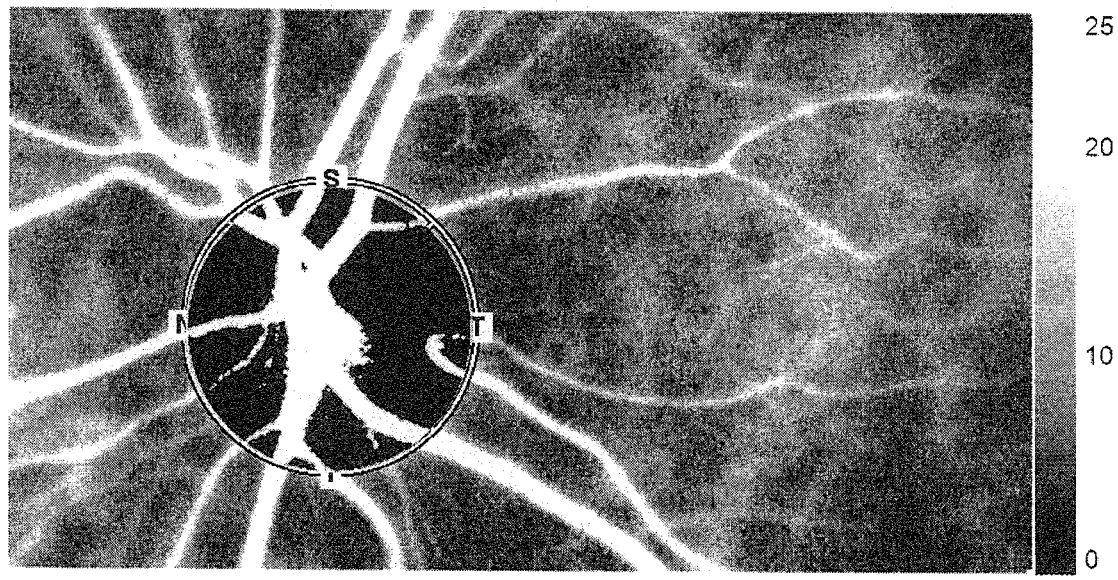
FIG. 24 exemplifies a map which is superimposed for display in the case where heartbeat detection was not performed successfully.

Further, when the heartbeat detection was performed successfully, the combined map-additional information map superimposing section 37 may superimpose a plurality of maps on the combined map, the plurality of maps including the waveform map in which the hemodynamics are represented by the waveform numerical values, the separation map (see FIG. 21 for the conventional technique) in which region information is added, etc.

Figure 3:
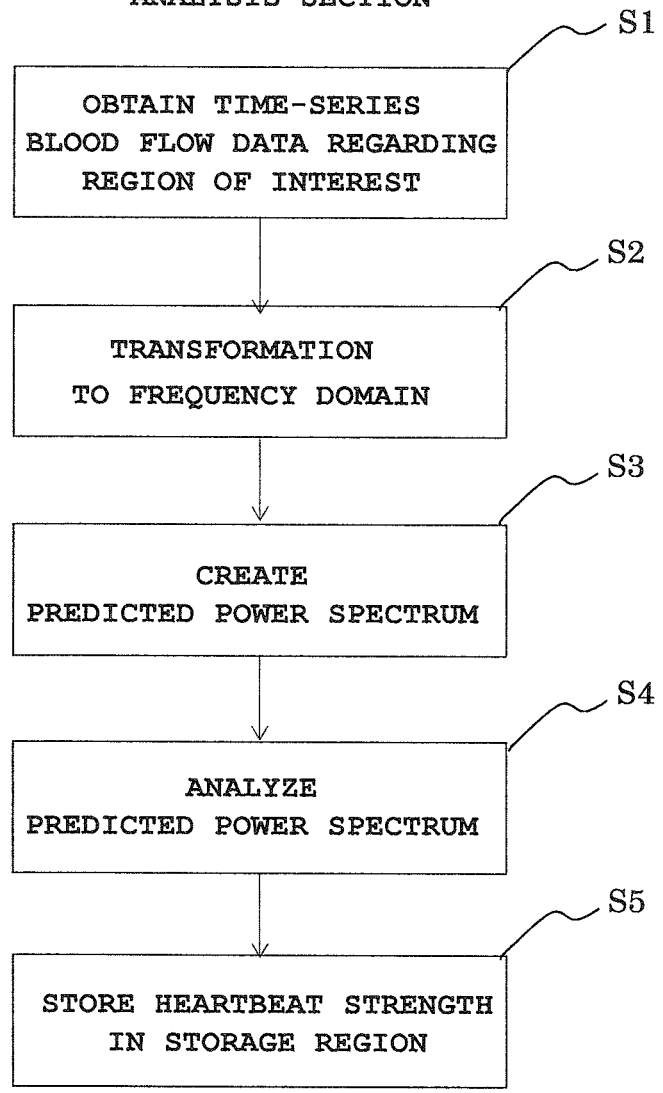
FIG. 3 shows a flowchart showing an example of computation performed by a blood flow power spectrum model analysis section.

Next, the flow of computation performed inside the blood flow power spectrum model analysis section 39 for computing the heartbeat strength will be described in more detail through use of the flowchart of FIG. 3.

First, in S1, the time-series blood flow data for the region of interest are obtained. The time-series blood flow data are obtained by the method described above. The time-series blood flow data may be data which lack some maps. The data are not required to be at equal intervals along the time axis. To n time-series blood flow data Y (y1, y2, . . . , yn), time information pieces T (t1, t2, . . . , tn) representing the times from the leading (first) map are added.

In general, when time-series data is Fourier-transformed, a power spectrum is obtained. Since the heartbeat strength is calculated on the basis of the power spectrum, creation of the power spectrum is necessary. In S2, the following matrix for Fourier series expansion into the frequency domain is calculated on the basis of the time information created in S1 as shown in Formula 1.

$$F = \begin{pmatrix} \sin(2\pi t_1 f_1) & \sin(2\pi t_1 f_2) & \ldots & \sin(2\pi t_1 f_M) & \cos(2\pi t_1 f_1) & \cos(2\pi t_1 f_2) & \ldots & \cos(2\pi t_1 f_M) \\ \sin(2\pi t_2 f_1) & \sin(2\pi t_2 f_2) & \ldots & \sin(2\pi t_2 f_M) & \cos(2\pi t_2 f_1) & \cos(2\pi t_2 f_2) & \ldots & \cos(2\pi t_2 f_M) \\ & & & \vdots & & & & \\ \sin(2\pi t_n f_1) & \sin(2\pi t_n f_2) & \ldots & \sin(2\pi t_n f_M) & \cos(2\pi t_n f_1) & \cos(2\pi t_n f_2) & \ldots & \cos(2\pi t_n f_M) \end{pmatrix}$$

[Formula 1]

In Formula 1, M is the frequency division number of the power spectrum and, for example, 100 may be set as the frequency division number. Also, f1, f2, . . . , fM are frequency elements of the power spectrum, and, for example, 0.1 Hz, 0.2 Hz, . . . , 10 Hz may be set as the frequency elements.

The time-series blood flow data is represented as follows through use of the matrix for Fourier series expansion created in S2.

$$Y = FX \quad \text{[Formula 2]}$$

In Formula 2, X is the vector of coefficients for each frequency element of the power spectrum and is composed of 2M elements as follows.

$$X = (a_1, a_2, \ldots a_M, b_1, b_2, \ldots, b_M) \quad \text{[Formula 3]}$$

In S3, the power spectrum is created from the time information transformed into the frequency domain and the time-series blood flow data. In the power spectrum of the time-series blood flow data of the region of interest, the power increases at a particular frequency. For example, in the case where the blood flow near the surface of a foot is measured, in a region where pulsations appear well, the power increases at a frequency in synchronous with the heart rate or at a frequency equal to or lower than 0.5 Hz where pulsations occur under the control of the sympathetic nerve system or the parasympathetic nerve system. The signals of these frequencies relating to the organism are considered to be sparse. The term "sparse" used herein refers to a state in which most frequency components on the power spectrum are approximately zero and only meaningful signal components, such as the pulsation signal and the signals of the sympathetic nerve system and the parasympathetic nerve system, appear. Since the power spectrum is sparse, the power spectrum can be predicted from the limited time-series blood flow data.

In the case where the power spectrum is sparse, an optimum predicted power spectrum can be created through use of, for example, a LASSO (least absolute shrinkage and selection operator) method or a different regression algorism such as Redge regression.

In general, calculation of the power spectrum is performed by obtaining time-series data for each measurement point, not the averaged blood flow value within the region of interest, and performing Fourier transformation. Therefore, time-series data obtained through measurement for a long period of time have been needed. For example, in the measurement for obtaining the power spectrum of an electrocardiogram, electrocardiograph data are obtained during a period of 100 to 600 beats, and Fourier transformation is performed for the obtained data for frequency analysis. Creation of the predicted power spectrum does not require a measurement performed for a long period of time unlike the conventional technique. A power spectrum from a low frequency of about 0.1 Hz to, for example, 100 Hz can be predicted on the basis of time-series blood flow data obtained during a short period of about 4 sec, whereby a frequency distribution can be obtained. In order to predict the power spectrum and obtain the frequency distribution, for example, LASSO or a like method (see Example 1) can be used.

The series of coefficients of the obtained optimal predicted power spectrum are defined as follows.

$$\hat{X} = (a_1, a_2, \ldots, a_M, b_1, b_2, \ldots, b_M) \quad \text{[Formula 4]}$$

A predicted power spectrum P(f) is created using the following equation.

$$P(f_i) = \sqrt{a_i^2 + b_i^2}$$

The total number of i is the frequency division number, and for example, i=1, 2, . . . 100.

Next, in S4, the predicted power spectrum obtained in S3 is analyzed, and one heartbeat strength is calculated. The heartbeat strength is a numerical value calculated on the basis of the predicted power spectrum, and, for example, is calculated by the following formula.

$$BS = C \times \max_i P(f_i) \quad \text{[Formula 5]}$$

Here, fi which satisfies BS will be referred to as the frequency corresponding to the heartbeat strength. C is a constant of proportionality for adjusting the scale of the heartbeat strength.

The heartbeat strength can be obtained from one, two or more frequency ranges set in advance. For example, the frequency ranges may be 0.05 Hz to 0.15 Hz and 0.15 Hz to 0.40 Hz. Other methods of computing the heartbeat strength include a method of obtaining the average value of the predicted power spectrum, a method of obtaining the local area of a peak of the distribution of a power spectrum having a mode, and a method of integrating values within a frequency range set in advance. Any of these methods may be employed.

In S5, the heartbeat strength which is the result of the analysis in S4 and the frequency corresponding to the heartbeat strength can be stored in the storage section for each region of interest. Since the heartbeat strength calculated once and the frequency corresponding to the heartbeat strength are stored in the storage region, there is a merit that it is unnecessary to calculate the heartbeat strength every time the region of interest is changed. When necessary, the heartbeat strength information of each region of interest can be transferred from the blood flow power spectrum model analysis section 39 to the heartbeat strength map creation section 40.

In the case where the blood flow waveform has a shape which is synchronous with pulsations, a value obtained by multiplying the frequency corresponding to the heartbeat strength stored in S5 by 60 becomes equal to the heart rate. For example, in the case where the region of interest is a region of the skin surface which involves arterial pulsations, the frequency corresponding to the heartbeat strength is 0.8 Hz to 1.5 Hz in the case of ordinary adults, because the heart rate is 50 to 90 in the case of ordinary adults.

In the case where the region of interest is a region which does not include many subcutaneous small arteries or the like and in which the peripheral blood flow is predominant, no pulsation is detected, and the frequency corresponding to the heartbeat strength becomes less than 0.5 Hz in many cases. There is a report stating that the power in this low frequency region represents the degree of activity of the sympathetic nerve system and the parasympathetic nerve system, and there is a high degree of possibility that, for a measurement target, such as a human, an animal, or the like, the state of activity of the nerve system in the peripheral region can be determined through use of the heartbeat strength.

The studies performed by the present inventors reveal that a power spectrum can be predicted from data during a period of 2 sec or longer; i.e., data of about 60 frames (in the case where a sold-state imaging device having a speed of 30 frames per sec is used). The optimum number of frames for calculation of the heartbeat strength performed through use of the apparatus developed by the present inventors is the number of frames of time-series blood flow data obtained during a period of about 4 sec. The heartbeat strength from which the hemodynamics of the peripheral blood flow can be grasped is obtained from data of 120 frame of images. When the period of the time-series blood flow variation becomes about 6 sec, the signal intensity of the sympathetic nerve system or the parasympathetic nerve system tends to become stronger than the blood flow change which occurs in synchronism with heartbeats and the power for discriminating the dynamics of the peripheral blood flow tends to become weaker.

The number of the heartbeat strengths created by the blood flow power spectrum model analysis section 39 for the regions of interest is equal to the number of the regions of interest, and the heartbeat strengths correspond to the regions of interest on the two-dimensional map. In the heartbeat strength map creation section 40, an empty virtual map is created, and the numerical values of the heartbeat strengths corresponding to the combined map are depicted at corresponding positions on the virtual map. In order to improve the visibility of the numerical values, a graph, such as a bar graph, from which the numerical values can be checked with improved visibility may be depicted near or within the regions of interest.

Example 1

A method of creating the predicted power spectrum through use of the LASSO method will be described as an example. The time-series blood flow data and the series of coefficients of the optimal predicted power spectrum can be represented by the following model function.

[Formula 6]
When the time-series blood flow data is represented by $Y \in R$ and the series of coefficients of the optimal predicted power spectrum is represented by $X \in R^P$, $$\hat{X} = \arg\min_{x} [[Y - FX]]_2^2 + \lambda [[X]]_1$$

where $\arg\min_x [[Y-FX]]_2^2$ is x when the function $[[Y-FX]]_2^2$ assumes the minimum value.

[Formula 7]
When $g=Y-FX$, $[[g]]_2^2$ means the square of the secondary norm and an equation of $[[g]]_2^2 = (\Sigma_i^{2M} |g_i|^2)^{2/2}$ stands. $[[X]]_1$ is the primary norm, and an equation of $[[X]]_1 = (\Sigma_i^{2M} |x_i|)$ stands.

The series of coefficients of the optimal predicted power spectrum can be solved by solving the minimization problem which satisfies Formula 6 and Formula 7. FIG. 7 shows an example of a feasible code (for example, written by R programming language) for solving the minimization problem of the LASSO method.

Example 2

In order to show an effective example of the present invention, the hemodynamics imaging and analyzing apparatus described herein was actually fabricated and the blood flow of a foot of a gout suffering patient (an example of a patient having a disease at his/her foot) was actually measured. FIG. 6 shows the results of the measurement. The patient feels a pain at an inflamed region of the left foot. The higher the degree of whiteness, the higher the blood flow value, and the higher the degree of blackness, the lower the blood flow value. Two circular regions of interest are set. The region of interest 1 is a region where inflammation is severe, and the region of interest 2 is a region where inflammation is not observed so much.

Figure 8:
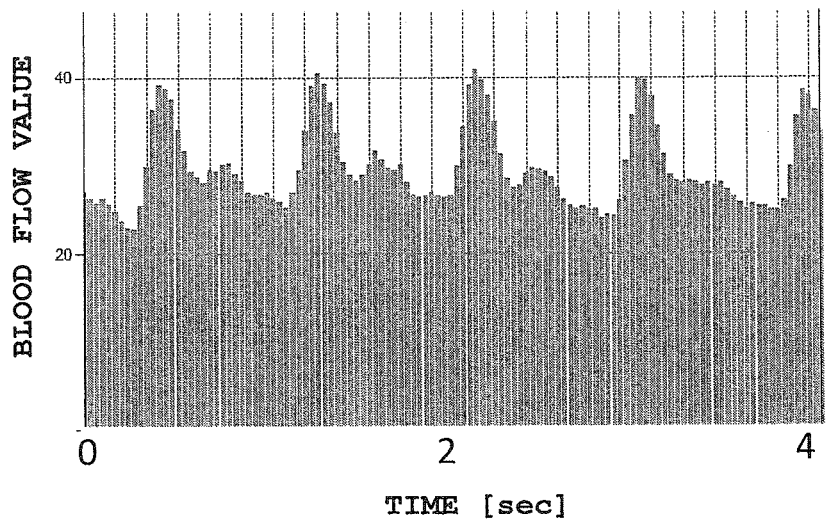
FIG. 8 is an example of time-series blood flow data extracted from a region 1 of FIG. 6 and shown in the form of a graph.

FIG. 8 is a chart in which the time-course changes of the blood flow value of the region of interest 1 are plotted and which shows changes in the blood flow value during a period of 4 sec. This chart shows that, as a result of the severe inflammation, the affected area is swollen, the blood flow value is large due to the influence of the inflammatory action, and the blood flow greatly changes in synchronism with pulsations. The blood flow waveform has a bimodal dynamic change in which the blood flow value sharply increases in the contraction phase, then decreases temporarily, and again increases.

Figure 9:
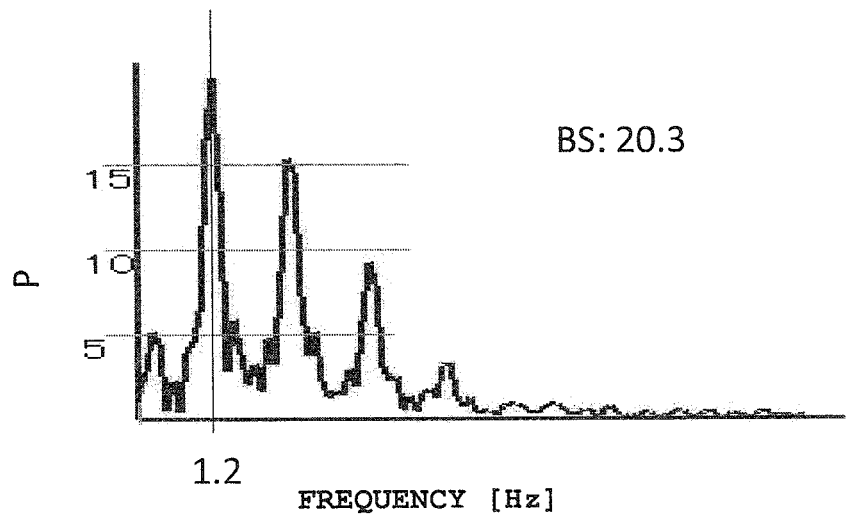
FIG. 9 is an example of a predicted power spectrum created from the time-series blood flow data extracted from the region 1 of FIG. 6.

FIG. 9 shows the power spectrum obtained on the basis of the signal of FIG. 8 through use of the function of the present invention. The graph shows that the frequency at which the power assumes the maximum value within the power spectrum (the frequency corresponding to the heartbeat strength) is 1.2 Hz. This result coincided with the output of the blood flow power spectrum model analysis section. Since the heart rate is 72, it is predicted that the signal is in synchronisms with pulsations. The heartbeat strength calculated simultaneously was BS 20.3. BS (arbitrary unit) means the maximum value of the power calculated on the basis of the power spectrum. The vertical axis of the graph shows the power of the power spectrum.

The waveform of FIG. 8 has a bimodal dynamic change. In the bimodal signal, other peaks were present at higher frequencies. However, when the power spectrum is observed, it is found that the power of the signal changing in synchronism with pulsations are stronger. The present example is one example in which the obtained heartbeat strength can be calculated more appropriately as an index of pulsation-induced dynamics.

Figure 10:
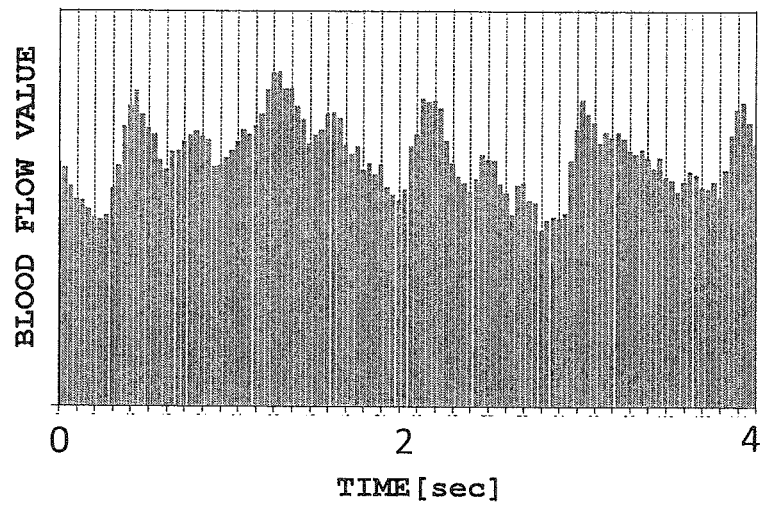
FIG. 10 is an example of time-series blood flow data extracted from a region 2 of FIG. 6 and shown in the form of a graph.

Meanwhile, FIG. 10 is a chart in which the time-course changes of the blood flow value of the region of interest 2 are plotted. The time-course changes in FIG. 10 are milder that the time-course changes in FIG. 8 which shows the time-course changes of the blood flow value of the region of interest 1. That is, the rising of pulsation is mild, the degree of steepness of the falling after the peak is less than that in FIG. 8, and the blood flow value decreases mildly after the peak.

Figure 11:
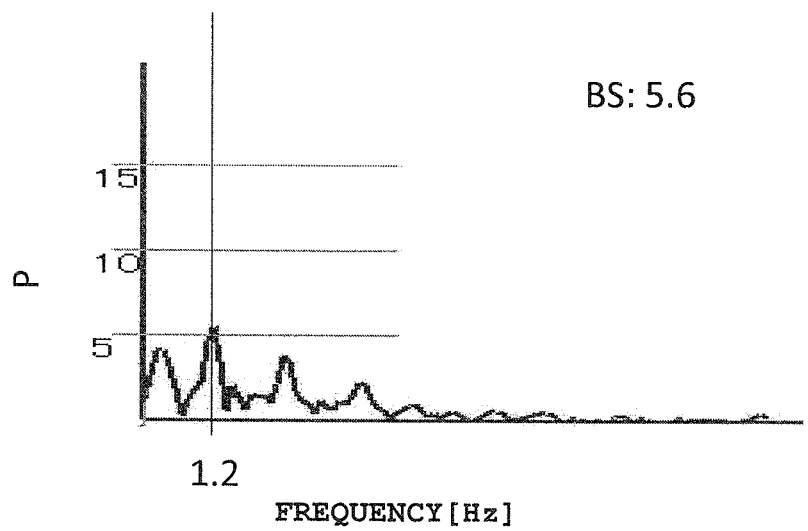
FIG. 11 is an example of a predicted power spectrum created from the time-series blood flow data extracted from the region 2 of FIG. 6.

FIG. 11 shows the power spectrum of the region of interest 2. The frequency corresponding to the heartbeat strength was calculated to be 1.2 Hz, and the heartbeat strength was calculated to be 5.6. The power synchronous with pulsations was smaller than that in the region of interest 1. A person having experienced swelling of a part of the body has sensually experienced that large pulses (=beats) occur in synchronism with pulsations. This case is one example in which the swollen portion (the region of interest 1) and the unswollen portion (the region of interest 2) can be compared in terms of the degree of beating, through use of the heartbeat strength which is an objective index, although the swollen portion and the unswollen portion are present in the same foot.

Figure 12:
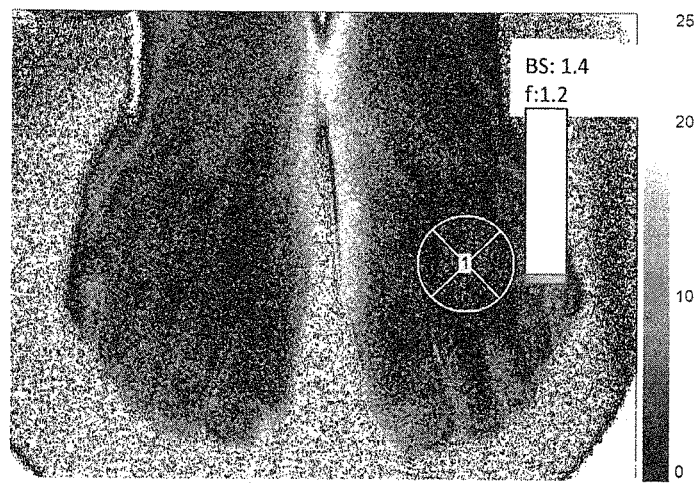
FIG. 12 is an example of a map in which a combined map and a heartbeat strength map of a gout suffering patient after remission are superimposed.
Figure 13:
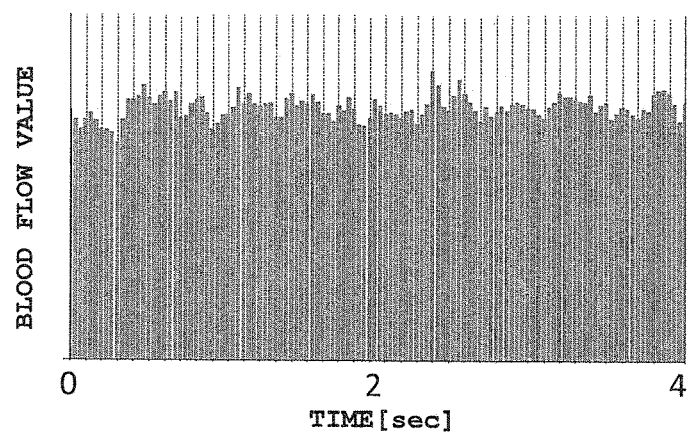
FIG. 13 is an example of time-series blood flow data extracted from a region 1 of FIG. 12 and shown in the form of a graph.
Figure 14:
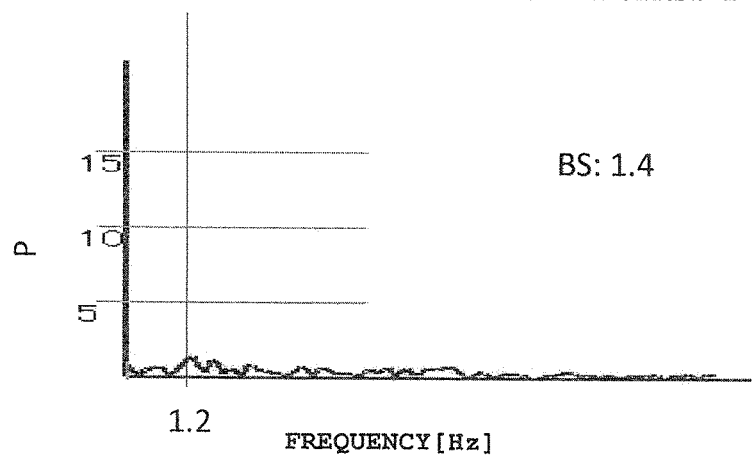
FIG. 14 is an example of a predicted power spectrum created from the time-series blood flow data extracted from the region 1 of FIG. 12.
Figure 15:
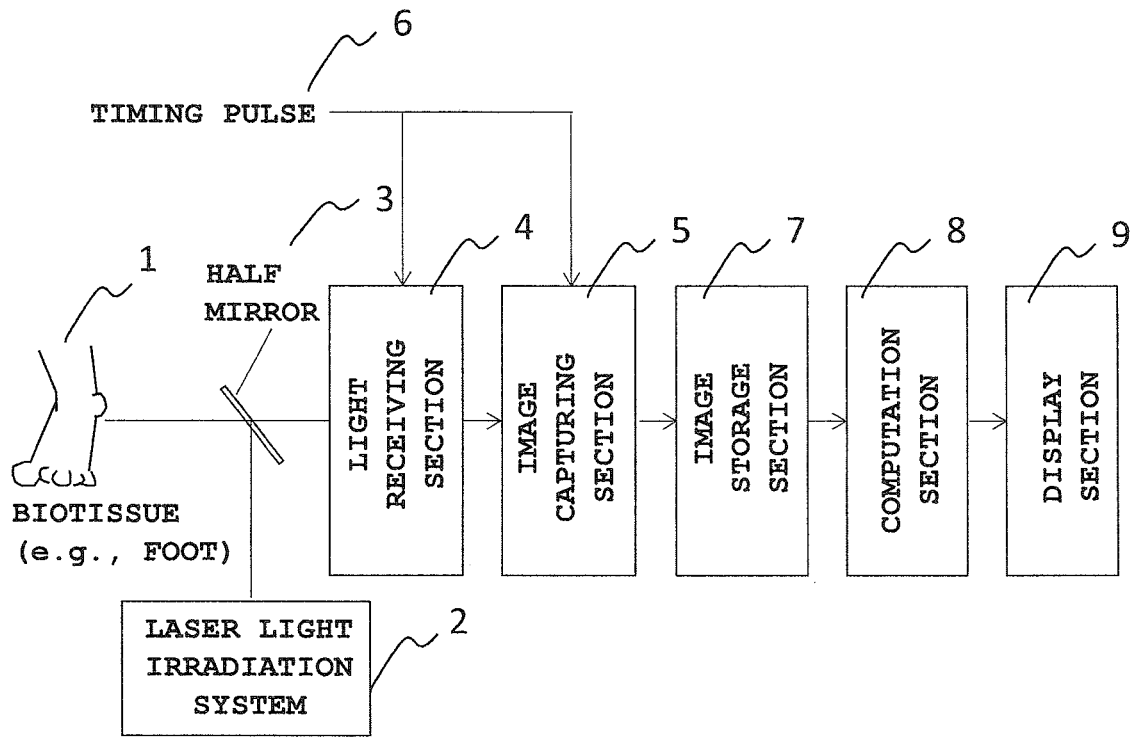
FIG. 15 shows an example of a schematic overall configurational diagram of a hemodynamics imaging and analyzing apparatus according to the conventional technique.

FIG. 12 shows a combined map obtained when the gout suffering patient of FIG. 6 has remitted later, and the result of measurement of the heartbeat strength. The region of interest 1 set at the time when the patient had gout was set as a region of interest 1 as in the case of FIG. 6. FIG. 13 shows the time-course changes of blood flow, and FIG. 14 shows the power spectrum.

The heartbeat strength of the region of interest 1 is 1.4. Since the inflammation observed when the maps of FIG. 6 were created has disappeared, pulsations are mild and hemodynamics are calm. Large blood flow variations synchronous with pulsations are not observed from the time-course changes of FIG. 13.

By nature, the blood flow on the peripheral side maintains a proper flow for the peripheral blood vessel network and a clear blood flow variation is hardly observed. This can be easily understood when the flow of water flowing from a small river to a large holding pond is considered. The larger the holding pond into which water flows, the greater the degree of gentleness and calmness of the waves on the surface of the holding pond. Meanwhile, when the current of the small river into the holding pond increases, the wave surfaces of the holding pond are agitated, whereby the degree of fluctuation of the surface increases and the power of the fluctuation increases.

Since the inflammation has disappeared and the degree of fluctuation of the blood flow has decreased before the point in time when the map of FIG. 12 was created through measurement, the blood flow into the foot is not hindered, and is adjusted to a proper level as can be understood from the numerical value of the heartbeat strength. Further, if a sufficient number of samples are obtained, it is possible to grasp and distinguish the peripheral hemodynamics by the heartbeat strength.

In the clinical field; in particular, in the field of plastic surgery, transplant of skin such as transplant of skin flap and skin graft is performed. The hemodynamics imaging apparatus configured on the basis of the present invention plays an important role for determination of the degree of settlement of the skin. Since the settlement of the skin requires the restoration of blood flow, grasping the hemodynamics will certainly become important in the future. Since the measurement can be performed noninvasively, subjects have no pain. Also, since laser irradiation does not apply a large amount of energy to subjects, the laser irradiation does not impart severe damages to the subjects. This is also a great advantage.

Hitherto, the present inventors have developed blood flow imaging apparatuses which can measure the hemodynamics of the blood flow of the skin, the blood flow of the internal organs, or the blood flow of the eyeground. As these products have the comparable specifications in terms of time resolution, the dynamics index can be digitized (represented by a numerical value), for a target whose blood flow can be observed in the same manner as for the skin blood flow. It can be easily imagined that the range of application of the present invention is not limited to the skin blood flow, and the heartbeat strength can be obtained from objects for which the blood flow measurement has been possible hitherto.

In this disclosure, only some embodiments have been described in detail above as examples; however, the embodiments may be modified in various ways without departing from the novel teachings and advantages of the present invention.

DESCRIPTION OF REFERENCE NUMERALS

20: biotissue
21: laser light irradiation system
22: half mirror
23: light receiving section
24: image capturing section
25: timing pulse
26: image storage section
27: computation section
28: display section
29: blood flow analysis section
30: heartbeat analysis section
31: heartbeat map creation section
32: combined map creation section
33: waveform numerical value creation section
34: waveform map creation section
35: surface layer-background separation section
36: separation map creation section
37: combined map-additional information map superimposing section
38: heartbeat strength computation section
39: blood flow power spectrum model analysis section
40: heartbeat strength map creation section

The invention claimed is:
1. A hemodynamics imaging and analyzing method comprising:
applying laser light to a biotissue including blood cells;
converting a reflection light from the biotissue into an electric signal and providing the electric signal as an image signal as output;
successively capturing a plurality of images based on the image signal;
storing the plurality of images;
computing a blood flow speed within the biotissue from time-course changes of corresponding pixels of the plurality of images stored; and
displaying, as a blood flow map, a two-dimensional distribution which is a result of computing the blood flow speed;

obtaining, from time-course changes of the blood flow map obtained as a result of computing the blood flow speed, a signal intensity at a fundamental frequency determined from time-series blood flow data within a region of interest, and calculating a heartbeat strength which represents a strength of heartbeats based on the signal intensity;

transforming the time-course changes of the blood flow map into a frequency domain through Fourier series expansion;

predicting a power spectrum on the basis of the blood flow data transformed into the frequency domain;

determining as the fundamental frequency, a frequency at which power becomes maximum within a distribution of the predicted power spectrum, obtaining a signal intensity corresponding thereto, and calculating the heartbeat strength;

creating a heartbeat strength map in which a strength of pulsation is mapped; and displaying the heartbeat strength map.

\* \* \* \* \*